US009499870B2

(12) United States Patent
Babiarz et al.

(10) Patent No.: US 9,499,870 B2
(45) Date of Patent: Nov. 22, 2016

(54) CELL FREE DNA DIAGNOSTIC TESTING STANDARDS

(71) Applicant: Natera, Inc., San Carlos, CA (US)

(72) Inventors: Joshua Babiarz, Castro Valley, CA (US); Bernhard Zimmermann, San Mateo, CA (US)

(73) Assignee: Natera, Inc., San Carlos, CA (US)

( * ) Notice: Subject to any disclaimer, the term of this patent is extended or adjusted under 35 U.S.C. 154(b) by 48 days.

(21) Appl. No.: 14/498,629

(22) Filed: Sep. 26, 2014

(65) Prior Publication Data

US 2015/0147815 A1    May 28, 2015

Related U.S. Application Data

(60) Provisional application No. 61/883,735, filed on Sep. 27, 2013, provisional application No. 61/978,658, filed on Apr. 11, 2014.

(51) Int. Cl.
*C12Q 1/68* (2006.01)
*C12N 15/10* (2006.01)

(52) U.S. Cl.
CPC ............ *C12Q 1/6886* (2013.01); *C12N 15/10* (2013.01); *C12Q 1/6806* (2013.01); *C12Q 1/6883* (2013.01); *C12Q 2521/301* (2013.01); *C12Q 2537/16* (2013.01); *C12Q 2545/113* (2013.01); *C12Q 2600/16* (2013.01); *C12Q 2600/166* (2013.01); *Y10T 436/10* (2015.01)

(58) Field of Classification Search
CPC .. C12N 15/10; C12Q 1/6806; C12Q 1/6883; C12Q 1/6886; C12Q 2521/301; C12Q 2537/16; C12Q 2545/113; C12Q 2600/16; C12Q 2600/166; Y10T 436/10
USPC ...... 436/8, 63, 94, 174; 435/4, 6.1, 6.14, 29, 435/325, 366, 372
See application file for complete search history.

(56) References Cited

U.S. PATENT DOCUMENTS

| | | |
|---|---|---|
| 5,635,366 A | 6/1997 | Cooke et al. |
| 5,716,776 A | 2/1998 | Bogart |
| 5,753,467 A | 5/1998 | Jensen et al. |
| 5,824,467 A | 10/1998 | Mascarenhas |
| 5,860,917 A | 1/1999 | Comanor et al. |
| 5,972,602 A | 10/1999 | Hyland et al. |
| 5,994,148 A | 11/1999 | Stewart et al. |
| 6,001,611 A | 12/1999 | Will |
| 6,025,128 A | 2/2000 | Veltri et al. |
| 6,108,635 A | 8/2000 | Herren et al. |
| 6,143,496 A | 11/2000 | Brown et al. |
| 6,180,349 B1 | 1/2001 | Ginzinger |
| 6,214,558 B1 | 4/2001 | Shuber et al. |
| 6,258,540 B1 | 7/2001 | Lo et al. |
| 6,300,077 B1 | 10/2001 | Shuber et al. |
| 6,440,706 B1 | 8/2002 | Vogelstein et al. |
| 6,479,235 B1 | 11/2002 | Schumm et al. |
| 6,489,135 B1 | 12/2002 | Parrott et al. |
| 6,720,140 B1 | 4/2004 | Hartley et al. |
| 6,807,491 B2 | 10/2004 | Pavlovic et al. |
| 6,852,487 B1 | 2/2005 | Barany et al. |
| 6,958,211 B2 | 10/2005 | Vingerhoets et al. |
| 7,035,739 B2 | 4/2006 | Schadt et al. |
| 7,058,517 B1 | 6/2006 | Denton et al. |
| 7,058,616 B1 | 6/2006 | Larder et al. |
| 7,218,764 B2 | 5/2007 | Vaisberg et al. |
| 7,297,485 B2 | 11/2007 | Bornarth et al. |
| 7,332,277 B2 | 2/2008 | Dhallan |
| 7,414,118 B1 | 8/2008 | Mullah et al. |
| 7,442,506 B2 | 10/2008 | Dhallan |
| 7,459,273 B2 | 12/2008 | Jones et al. |
| 7,645,576 B2 | 1/2010 | Lo et al. |
| 7,700,325 B2 | 4/2010 | Cantor et al. |
| 7,718,367 B2 | 5/2010 | Lo et al. |
| 7,718,370 B2 | 5/2010 | Dhallan |
| 7,727,720 B2 | 6/2010 | Dhallan |
| 7,805,282 B2 | 9/2010 | Casey |
| 7,838,647 B2 | 11/2010 | Hahn et al. |
| 7,888,017 B2 | 2/2011 | Quake |
| 8,008,018 B2 | 8/2011 | Quake et al. |
| 8,024,128 B2 | 9/2011 | Rabinowitz |
| 8,137,912 B2 | 3/2012 | Kapur et al. |

(Continued)

FOREIGN PATENT DOCUMENTS

| | | |
|---|---|---|
| EP | 1524321 A1 | 4/2005 |
| EP | 1524321 B1 | 7/2009 |

(Continued)

OTHER PUBLICATIONS

Forshew et al. Science Translational Medicine, vol. 4, issue 136, May 30, 2012, pp. 1-12.*
"Blast of AAAAAAAAATTTAAAAAAAAATTT" (http://blast.ncbi.nlm.nih.gov/Blast.cgi), downloaded May 4, 2015.
"CompetitivePCR Guide," TaKaRa Biomedicals, Lit. # L0126 Rev. 8/99, 9 pgs.
"db SNP rs2056688" (http://www.ncbi.nlm.nih.gov/projects/SNP/snp_ref.cgi?rs=2056688), downloaded May 4, 2015.
Declaration by Dr. Zimmerman of Oct. 30, 2014 filed in U.S. Appl. No. 14/044,434.
European Application No. 014198110, European Search Report Mailed Apr. 28, 2015, 3 pages.
"Finishing the Euchromatic Sequence of the Human Genome", Nature vol. 431,(Oct. 21, 2004), 931-945.

(Continued)

*Primary Examiner* — Maureen Wallenhorst
(74) *Attorney, Agent, or Firm* — Anton Bokal

(57) ABSTRACT

Embodiments of the invention include methods and compositions for producing proficiency testing standards for noninvasive prenatal genetic diagnostics and for the detection and monitoring of cancer. The compositions can include a plurality of different nucleosomal DNA fragments derived from either primary cells or cell lines. The amount of the different nucleosomal DNA fragments can be varied so as to simulate naturally occurring cell free DNA samples obtained from the blood of the pregnant woman or naturally occurring cell free DNA samples obtained from the blood of cancer patients.

18 Claims, 4 Drawing Sheets

(56) References Cited

U.S. PATENT DOCUMENTS

| | | |
|---|---|---|
| 8,168,389 B2 | 5/2012 | Shoemaker et al. |
| 8,195,415 B2 | 6/2012 | Fan et al. |
| 8,296,076 B2 | 10/2012 | Fan et al. |
| 8,304,187 B2 | 11/2012 | Fernando |
| 8,318,430 B2 | 11/2012 | Chuu et al. |
| 8,467,976 B2 | 6/2013 | Lo et al. |
| 8,515,679 B2 | 8/2013 | Rabinowitz et al. |
| 8,532,930 B2 | 9/2013 | Rabinowitz et al. |
| 8,682,592 B2 | 3/2014 | Rabinowitz et al. |
| 8,825,412 B2 | 9/2014 | Rabinowitz et al. |
| 2001/0053519 A1 | 12/2001 | Fodor et al. |
| 2002/0006622 A1 | 1/2002 | Bradley et al. |
| 2003/0009295 A1 | 1/2003 | Markowitz et al. |
| 2003/0065535 A1 | 4/2003 | Karlov et al. |
| 2003/0077586 A1 | 4/2003 | Pavlovic et al. |
| 2003/0101000 A1 | 5/2003 | Bader et al. |
| 2003/0228613 A1 | 12/2003 | Bornarth et al. |
| 2004/0033596 A1 | 2/2004 | Threadgill et al. |
| 2004/0137470 A1 | 7/2004 | Dhallan et al. |
| 2004/0197797 A1 | 10/2004 | Inoko et al. |
| 2004/0236518 A1 | 11/2004 | Pavlovic et al. |
| 2004/0259100 A1 | 12/2004 | Gunderson et al. |
| 2005/0009069 A1 | 1/2005 | Liu et al. |
| 2005/0049793 A1 | 3/2005 | Paterlini-Brechot |
| 2005/0123914 A1 | 6/2005 | Katz et al. |
| 2005/0142577 A1 | 6/2005 | Jones et al. |
| 2005/0144664 A1 | 6/2005 | Smith et al. |
| 2005/0164241 A1 | 7/2005 | Hahn et al. |
| 2005/0221341 A1 | 10/2005 | Shimkets et al. |
| 2005/0227263 A1 | 10/2005 | Green et al. |
| 2005/0250111 A1 | 11/2005 | Xie et al. |
| 2005/0255508 A1 | 11/2005 | Casey et al. |
| 2005/0272073 A1 | 12/2005 | Vaisberg et al. |
| 2006/0019278 A1 | 1/2006 | Lo et al. |
| 2006/0040300 A1 | 2/2006 | Dapprich et al. |
| 2006/0052945 A1 | 3/2006 | Rabinowitz et al. |
| 2006/0057618 A1 | 3/2006 | Piper et al. |
| 2006/0068394 A1 | 3/2006 | Langmore et al. |
| 2006/0088574 A1 | 4/2006 | Manning et al. |
| 2006/0099614 A1 | 5/2006 | Gill et al. |
| 2006/0121452 A1 | 6/2006 | Dhallan |
| 2006/0134662 A1 | 6/2006 | Pratt et al. |
| 2006/0141499 A1 | 6/2006 | Sher et al. |
| 2006/0210997 A1 | 9/2006 | Myerson et al. |
| 2006/0216738 A1 | 9/2006 | Wada et al. |
| 2006/0229823 A1 | 10/2006 | Liu |
| 2006/0281105 A1 | 12/2006 | Li et al. |
| 2007/0027636 A1 | 2/2007 | Rabinowitz |
| 2007/0059707 A1 | 3/2007 | Cantor et al. |
| 2007/0122805 A1 | 5/2007 | Cantor et al. |
| 2007/0178478 A1 | 8/2007 | Dhallan |
| 2007/0178501 A1 | 8/2007 | Rabinowitz et al. |
| 2007/0184467 A1 | 8/2007 | Rabinowitz et al. |
| 2007/0202525 A1 | 8/2007 | Quake et al. |
| 2007/0202536 A1 | 8/2007 | Yamanishi et al. |
| 2007/0207466 A1 | 9/2007 | Cantor et al. |
| 2007/0212689 A1 | 9/2007 | Bianchi et al. |
| 2007/0243549 A1 | 10/2007 | Bischoff |
| 2007/0259351 A1 | 11/2007 | Chinitz |
| 2008/0020390 A1 | 1/2008 | Mitchell |
| 2008/0026390 A1 | 1/2008 | Stoughton et al. |
| 2008/0038733 A1 | 2/2008 | Bischoff et al. |
| 2008/0070792 A1 | 3/2008 | Stoughton |
| 2008/0071076 A1 | 3/2008 | Hahn et al. |
| 2008/0085836 A1 | 4/2008 | Kearns et al. |
| 2008/0102455 A1 | 5/2008 | Poetter |
| 2008/0138809 A1 | 6/2008 | Kapur et al. |
| 2008/0182244 A1 | 7/2008 | Tafas et al. |
| 2008/0193927 A1 | 8/2008 | Mann et al. |
| 2008/0234142 A1 | 9/2008 | Lietz |
| 2008/0243398 A1 | 10/2008 | Rabinowitz et al. |
| 2009/0023190 A1 | 1/2009 | Lao et al. |
| 2009/0029377 A1 | 1/2009 | Lo et al. |
| 2009/0087847 A1 | 4/2009 | Lo et al. |
| 2009/0098534 A1 | 4/2009 | Weier et al. |
| 2009/0099041 A1 | 4/2009 | Church et al. |
| 2009/0176662 A1 | 7/2009 | Rigatti et al. |
| 2009/0221620 A1 | 9/2009 | Luke et al. |
| 2010/0035232 A1 | 2/2010 | Ecker et al. |
| 2010/0112575 A1 | 5/2010 | Fan et al. |
| 2010/0112590 A1 | 5/2010 | Lo et al. |
| 2010/0120038 A1 | 5/2010 | Mir et al. |
| 2010/0124751 A1 | 5/2010 | Quake et al. |
| 2010/0138165 A1 | 6/2010 | Fan et al. |
| 2010/0171954 A1 | 7/2010 | Quake et al. |
| 2010/0184069 A1 | 7/2010 | Fernando et al. |
| 2010/0184152 A1 | 7/2010 | Sandler |
| 2010/0196892 A1 | 8/2010 | Quake et al. |
| 2010/0203538 A1 | 8/2010 | Dube et al. |
| 2010/0216153 A1 | 8/2010 | Lapidus et al. |
| 2010/0248231 A1 | 9/2010 | Wei et al. |
| 2010/0255492 A1 | 10/2010 | Quake et al. |
| 2010/0256013 A1 | 10/2010 | Quake et al. |
| 2010/0285537 A1 | 11/2010 | Zimmermann |
| 2010/0291572 A1 | 11/2010 | Stoughton et al. |
| 2010/0323352 A1 | 12/2010 | Lo et al. |
| 2011/0033862 A1 | 2/2011 | Rabinowitz et al. |
| 2011/0039724 A1 | 2/2011 | Lo et al. |
| 2011/0086769 A1 | 4/2011 | Oliphant et al. |
| 2011/0092763 A1 | 4/2011 | Rabinowitz et al. |
| 2011/0105353 A1 | 5/2011 | Lo et al. |
| 2011/0151442 A1 | 6/2011 | Fan et al. |
| 2011/0178719 A1 | 7/2011 | Rabinowitz et al. |
| 2011/0201507 A1 | 8/2011 | Rava et al. |
| 2011/0224087 A1 | 9/2011 | Quake et al. |
| 2011/0246083 A1 | 10/2011 | Fan et al. |
| 2011/0251149 A1 | 10/2011 | Perrine et al. |
| 2011/0288780 A1 | 11/2011 | Rabinowitz et al. |
| 2011/0300608 A1 | 12/2011 | Ryan et al. |
| 2011/0318734 A1 | 12/2011 | Lo et al. |
| 2012/0003635 A1 | 1/2012 | Lo et al. |
| 2012/0034603 A1 | 2/2012 | Oliphant et al. |
| 2012/0122701 A1 | 5/2012 | Ryan et al. |
| 2012/0165203 A1 | 6/2012 | Quake et al. |
| 2012/0185176 A1 | 7/2012 | Rabinowitz et al. |
| 2012/0190020 A1 | 7/2012 | Oliphant et al. |
| 2012/0190021 A1 | 7/2012 | Oliphant et al. |
| 2012/0191358 A1 | 7/2012 | Oliphant et al. |
| 2012/0196754 A1 | 8/2012 | Quake et al. |
| 2012/0214678 A1 | 8/2012 | Rava et al. |
| 2012/0264121 A1 | 10/2012 | Rava et al. |
| 2012/0270212 A1 | 10/2012 | Rabinowitz et al. |
| 2013/0017549 A1 | 1/2013 | Hong |
| 2013/0024127 A1 | 1/2013 | Stuelpnagel |
| 2013/0034546 A1 | 2/2013 | Rava et al. |
| 2013/0060483 A1 | 3/2013 | Struble et al. |
| 2013/0069869 A1 | 3/2013 | Akao et al. |
| 2013/0090250 A1 | 4/2013 | Sparks et al. |
| 2013/0123120 A1 | 5/2013 | Zimmermann et al. |
| 2013/0178373 A1 | 7/2013 | Rabinowitz et al. |
| 2013/0190653 A1 | 7/2013 | Alvarez Ramos |
| 2013/0196862 A1 | 8/2013 | Rabinowitz et al. |
| 2013/0210644 A1 | 8/2013 | Stoughton et al. |
| 2013/0225422 A1 | 8/2013 | Rabinowitz et al. |
| 2013/0252824 A1 | 9/2013 | Rabinowitz |
| 2013/0253369 A1 | 9/2013 | Rabinowitz et al. |
| 2013/0261004 A1 | 10/2013 | Ryan et al. |
| 2013/0274116 A1 | 10/2013 | Rabinowitz et al. |
| 2013/0303461 A1 | 11/2013 | Iafrate et al. |
| 2013/0323731 A1 | 12/2013 | Lo et al. |
| 2014/0032128 A1 | 1/2014 | Rabinowitz et al. |
| 2014/0051585 A1 | 2/2014 | Prosen et al. |
| 2014/0065621 A1 | 3/2014 | Mhatre et al. |
| 2014/0087385 A1 | 3/2014 | Rabinowitz et al. |
| 2014/0094373 A1 | 4/2014 | Zimmermann et al. |
| 2014/0100126 A1 | 4/2014 | Rabinowitz |
| 2014/0100134 A1 | 4/2014 | Rabinowitz et al. |
| 2014/0141981 A1 | 5/2014 | Zimmermann et al. |
| 2014/0154682 A1 | 6/2014 | Rabinowitz et al. |
| 2014/0162269 A1 | 6/2014 | Rabinowitz |
| 2014/0193816 A1 | 7/2014 | Rabinowitz et al. |
| 2014/0206552 A1 | 7/2014 | Rabinowitz et al. |
| 2014/0256569 A1 | 9/2014 | Rabinowitz et al. |

(56) References Cited

U.S. PATENT DOCUMENTS

| | | |
|---|---|---|
| 2014/0329245 A1 | 11/2014 | Spier et al. |
| 2014/0336060 A1 | 11/2014 | Rabinowitz |
| 2015/0064695 A1 | 3/2015 | Katz et al. |

FOREIGN PATENT DOCUMENTS

| | | |
|---|---|---|
| GB | 2488358 | 8/2012 |
| JP | 2965699 | 8/1999 |
| JP | 2004502466 A | 1/2004 |
| JP | 2004533243 A | 11/2004 |
| JP | 2005514956 A | 5/2005 |
| JP | 2005160470 A | 6/2005 |
| WO | 179851 A1 | 10/2001 |
| WO | WO0190419 A2 | 11/2001 |
| WO | 0204672 A2 | 1/2002 |
| WO | 02055985 A2 | 7/2002 |
| WO | WO02076377 | 10/2002 |
| WO | WO03031646 A1 | 4/2003 |
| WO | 03050532 A1 | 6/2003 |
| WO | 03062441 A1 | 7/2003 |
| WO | 03102595 A1 | 12/2003 |
| WO | 03106623 A2 | 12/2003 |
| WO | 2004087863 A2 | 10/2004 |
| WO | 2005021793 A1 | 3/2005 |
| WO | 2005035725 A2 | 4/2005 |
| WO | 2005100401 A2 | 10/2005 |
| WO | 2005123779 A2 | 12/2005 |
| WO | 2007057647 A1 | 5/2007 |
| WO | 2007062164 A3 | 5/2007 |
| WO | WO2007070482 A2 | 6/2007 |
| WO | 2007132167 A2 | 11/2007 |
| WO | WO2007147074 A2 | 12/2007 |
| WO | 2008024473 A2 | 2/2008 |
| WO | 2008048931 A1 | 4/2008 |
| WO | 2008051928 A2 | 5/2008 |
| WO | 2008081451 A2 | 7/2008 |
| WO | 2008115497 A2 | 9/2008 |
| WO | 2008135837 A2 | 11/2008 |
| WO | 2008157264 A2 | 12/2008 |
| WO | 2009009769 A2 | 1/2009 |
| WO | 2009013492 A1 | 1/2009 |
| WO | 2009013496 A1 | 1/2009 |
| WO | 2009019215 A1 | 2/2009 |
| WO | 2009019455 A2 | 2/2009 |
| WO | 2009030100 A1 | 3/2009 |
| WO | 2009032779 A2 | 3/2009 |
| WO | 2009032781 A2 | 3/2009 |
| WO | 2009033178 A1 | 3/2009 |
| WO | 2009091934 A1 | 7/2009 |
| WO | 2009092035 A2 | 7/2009 |
| WO | 2009105531 A1 | 8/2009 |
| WO | 2009146335 A1 | 12/2009 |
| WO | 2010017214 A1 | 2/2010 |
| WO | WO2010075459 | 7/2010 |
| WO | 2011041485 A1 | 4/2011 |
| WO | 2011/057094 * | 5/2011 |
| WO | WO2011087760 | 7/2011 |
| WO | 2011146632 A1 | 11/2011 |
| WO | 2012071621 | 6/2012 |
| WO | 2012088456 A2 | 6/2012 |
| WO | WO2012083250 | 6/2012 |
| WO | 2012108920 A1 | 8/2012 |
| WO | 2013/030577 * | 3/2013 |
| WO | 2013052557 A2 | 4/2013 |
| WO | 2013130848 | 9/2013 |
| WO | 2014018080 | 1/2014 |

OTHER PUBLICATIONS

"FixedMedium, dictionary definition, Academic Press Dictionary of Science andTechnology", Retrieved from the Internet: <URL:www.credoreference.com/entry/apdst/fixed_medium>, 1996, 1 pg.

"GeneticsHome Reference", http://ghr.nlm.nih.gov/handbook/genomicresearch/snp, Feb. 28, 2014, 1-2.

"Guideline related to genetic examination", Societies Related to Genetic Medicine, Japanese Society for Genetic Counseling, Japanese Society for Gene Diagnosis and Therapy, Japan Society of Obstetrics an, 2003, 2-15.

"How ManyCarbs in a Potato?, [Online]", Retrieved from theInternet:<http://www.newhealthguide.org/How-Many-Carbs-In-A-Potato.html>, Nov. 1, 2014, 3 pgs.

"Ion Ampli Seq Comprehensive Cancer Panel, product brochure, Life TechnologiesCorporation. Retrieved from the Internet", <URL:https://tools.lifetechnologies.com/content/sfs/brochures/Ion_CompCancerPanel_Flyer.pdf>, 2012, 2 pgs.

"IonAmpliSeq Designer Provides Full Flexibility to Sequence Genes of Your Choice,product brochure, Life Technologies Corporation", Retrieved from the Internet<URL: http://tools.lifetechnologies.com/content/sfs/brochures/IonAmpliSeq_CustomPanels_AppNote_CO1.

Merriam-Webster.com (http://www.merriam-webster.com/dictionary/universal, downloaded Jul. 23, 2014).

"Multiplexing with RainDrop Digital PCR", RainDance Technologies, Application Note, 2013, 1-2.

"NucleicAcids, Linkers and Primers: Random Primers", New England BioLabs 1998/99Catalog, 1998, 121 and 284.

"PRIMER3, information sheet, Sourceforge.net. [retrieved on Nov. 12, 2012]. Retrieved from the Internet: <URL: http://primer3.sourceforge.net/>", 2009, 1 pg.

"www.fatsecret.com" (printed from internet Nov. 1, 2014).

Merriam-Webster (available at http://www.merriam-webster.com/medical/stimulant, accessed Mar. 14, 2016).

PRNewswire (Research Suggests Daily Consumption of Orange Juice Can Reduce Blood Pressure and May Provide Beneficial Effects to Blood Vessel Function: New Study Identified Health Benefits in Orange Juice, Dec. 8, 2010).

The Bump (Panorama Test, Jul. 1, 2013).

What to Expect (Weird Harmony results, May 1, 2015).

Wikipedia (available at https://en.wikipedia.org/wiki/Stimulant, accessed Mar. 14, 2016).

Abidi, S. et al., "Leveraging XML-based electronic medical records to extract experiential clinical knowledge: An automated approach to generate cases for medical case-based reasoning systems", International Journal of Medical Informatics, 68(1-3), 2002, 187-203.

Agarwal, Ashwin. et al., "Commercial Landscape of Noninvasive Prenatal Testing in the United States", Prenatal Diagnosis,33, 2013, 521-531.

Alkan, Can et al., "Personalized Copy Number and Segmental Duplication Maps Using Next-Generation Sequencing", Nature Genetics, 41, 10, 2009, 1061-1068.

Allaire, F R., "Mate selection by selection index theory", Theoretical Applied Genetics, 57(6), 1980, 267-272.

Allawi, Hatim T. et al., "Thermodynamics of internal C•T Mismatches in DNA", Nucleic Acids Research, 26 (11), 1998, 2694-2701.

Aoki, Yasuhiro, "Statistical and Probabilistic Bases of Forensic DNA Testing", The Journal of the Iwate Medical Association, 2002, vol. 54, p. 81-94.

Ashoor, Ghalia et al., "Fetal Fraction in Maternal Plasma Cell-Free DNA at 11-13 Weeks' Gestation: Effect of Maternal and Fetal Factors", Fetal Diagnosis Therapy, 2012, 1-7.

Ashoor, Ghalia. et al., "Chromosome-Selective Sequencing of Maternal Plasma Cell-Free DNA for First-Trimester Detection of Trisomy 21 and Trisomy 18", American Journal of Obstetrics & Gynecology, 206, 2012, 322.e1-322.e5.

Bada, Michael A. et al., "Computational Modeling of Structural Experimental Data", Methods in Enzymology,317, 2000, 470-491.

Beaumont, Mark A et al., "The Bayesian Revolution in Genetics", Nature Reviews Genetics, 5, 2004, 251-261.

Beer, Alan E. et al., "The Biological Basis of Passage of Fetal Cellular Material into the Maternal Circulation", Annals New York Academy of Sciences, 731, 1994, 21-35.

Beerenwinkel, et al., "Methods for Optimizing Antiviral Combination Therapies", Bioinformatics, 19(1), 2003, i16-i25.

Beerenwinkel, N. et al., "Geno2pheno: estimating phenotypic drug resistance from HIV-1 genotypes", Nucleic Acids Research, 31(13), 2003, 3850-3855.

(56) References Cited

OTHER PUBLICATIONS

Benn, P. et al., "Non-Invasive Prenatal Testing for Aneuploidy: Current Status and Future Prospects", Ultrasound Obstet Gynecol, 42, 2013, 15-33.
Benn, P. et al., "Non-Invasive prenatal Diagnosis for Down Syndrome: the Paradigm Will Shift, but Slowly", Ultrasound Obstet. Gynecol., 39, 2012, 127-130.
Bentley, David R. et al., "Accurate Whole Human Genome Sequencing Using Reversible Terminator Chemistry", Nature, 456, 6, 2008, 53-59.
Bermudez, M. et al., "Single-cell sequencing and mini-sequencing for preimplantation genetic diagnosis", Prenatal Diagnosis, 23, 2003, 669-677.
Bevinetto, Gina, Bevinetto (5 Foods All Pregnant Women Need, American Baby, available at http://www.parents.com/pregnancy/mybody/nutrition/5greatpregnancyfoods/, Apr. 15, 2008).
Bianchi, D W. et al., "Fetal gender and aneuploidy detection using fetal cells maternal blood: analysis of NIFTY I data", Prenat Diagn 2002; 22, 2002, 609-615.
Birch, Lyndsey et al., "Accurate and Robust Quantification of Circulating Fetal and Total DNA in Maternal Plasma from 5 to 41 Weeks of Gestation", Clinical Chemistry, 51(2), 2005, 312-320.
Bisignano, et al., "PGD and Aneuploidy Screening for 24 Chromosomes: Advantages and Disadvantages of Competing Platforms", Reproductive BioMedicine Online, 23, 2011, 677-685.
Bodenreider, O., "The Unified Medical Language System (UMLS): Integrating Biomedical Terminology", Nucleic Acids Research, 32, (Database issue), 2004, D267-D270.
Breithaupt, Holger, "The Future of Medicine", EMBO Reports, 21(61), 2001, 465-467.
Brownie, Jannine et al., "The Elimination of Primer-Dimer Accumulation in PCR", Nucleic Acids Research, 25(16), 1997, 3235-3241.
Cairns, Paul et al., "Homozygous Deletions of 9p21 in Primary Human Bladder Tumors Detected by Comparative Multiplex Polymerase Chain Reaction", Cancer Research, 54, 1994, 1422-1424.
Caliendo, Angela, "Multiplex PCR and Emerging Technologies for the Detection of Respiratory Pathogens", Clinical Infectious Diseases, 52(4), 2011, S326-S330.
Carnevale, Alessandra et al., "Attitudes of Mexican Geneticists Towards Prenatal Diagnosis and Selective Abortion", American Journal of Medical Genetics, 75, 1998, 426-431.
Chen, E. et al., "Noninvasive Prenatal Diagnosis of Fetal Trisomy 18 and Trisomy 13 by Maternal Plasma DNA Sequencing", PLoS One, 6 (7), e21791, 2011, 7 pgs.
Chetty, Shilpa et al., "Uptake of Noninvasive Prenatal Testing (NIPT) in Women Following Positive Aneuploidy Screening", Prenatal Diagnosis,33, 2013, 542-546.
Chiu, R. et al., "Non-Invasive Prenatal Assessment of Trisomy 21 by Multiplexed Maternal Plasma DNA Sequencing: Large Scale Validity Study", BMJ, 342, c7401, 2011, 9 pgs.
Chiu, Rossa W. et al., "Effects of Blood-Processing Protocols on Fetal and Total DNA Quantification in Maternal Plasma", Clinical Chemistry, 47(9), 2001, 1607-1613.
Chiu, Rossa W.K et al., "Maternal Plasma DNA Analysis with Massively Parallel Sequencing by Litigation for Noninvasive Prenatal Diagnosis of Trisomy 21", Clinical Chemistry, 56, 3, 2010, 459-463.
Chiu, Rossa W.K et al., "Noninvasive Prenatal Diagnosis of Fetal Chromosomal Aneuploidy by Massively Parallel Genomic Sequencing of DNA in Maternal Plasma", PNAS, 105, 51 (with Supporting Information), 2008, 23.
Chiu, Rossa W.K. et al., "Non-Invasive Prenatal Diagnosis by Single Molecule Counting Technologies", Trends in Genetics, 25 (7), 2009, 324-331.
Chu, T. et al., "Statistical Considerations for Digital Approaches to Non-Invasive Fetal Genotyping", Bioinformatics (Advance Access publication), 26 (22), 2010, 2863-2866.

Chu, Tianjiao et al., "Statistical Model for Whole Genome Sequencing and its Application to Minimally Invasive Diagnosis of Fetal Genetic Disease", Bioinformatics, 25(10), 2009, 1244-1250.
Chu, Tianjiao et al., "A Novel Approach Toward the Challenge of Accurately Quantifying Fetal DNA in Maternal Plasma", Prenatal Diagnosis,30, 2010, 1226-1229.
Cole, Neal W. et al., "Hyperglycemia-Induced Membrane Lipid Peroxidation and Elevated Homocysteine Levels Are Poorly Attenuated by Exogenous Folate in Embryonic Chick Brains", Comparative Biochemistry and Physiology, Part B, 150, 2008, 338-343.
Colella, S. et al., "QuantiSNP: an Objectives Bayes Hidden-Markov Model to Detect and Accurately Map Copy Number Variation Using SNP Genotyping Data", Nucleic Acids Research, 35 (6), 2007, 2013-2025.
Cossu, Gianfranco et al., "Rh D/d Genotyping by Quantitative Polymerase Chain Reaction and Capillary Zone Electrophoresis", Electrophoresis, 17, 1996, 1911-1915.
Coyle, J. F. et al., "Standards for detailed clinical models as the basis for medical data exchange and decision support", International Journal of Medical Informatics, 69(2-3), 2003, 157-174.
Cross, Jillian et al., "Resolution of trisomic mosaicism in prenatal diagnosis: estimated performance of a 50K SNP microarray", Prenat Diagn 2007; 27, 2007, 1197-1204.
D'Aquila, Richard et al., "Maximizing sensitivity and specificity of PCR by pre-amplification heating", Nucleic Acids Research, 19(13), 1991, p. 3749.
Daruwala, Raoul-Sam et al., "A Versatile Statistical Analysis Algorithm to Detect Genome Copy Number Variation", PNAS, 101(46), 2004, 16292-16297.
De Vries, et al., "Diagnostic genome profiling in mental retardation", Am J Hum Genet, 77, published online Aug. 30, 2005, 2005, 606-616.
DeAngelis, M. et al., "Solid-phase Reversible Immobilization for the Isolation of PCR Products", Nucleic Acids Research, 23 (22), 1995, 4742-4743.
Devaney, S. et al., "Noninvasive Fetal Sex Determination Using Cell-Free Fetal DNA: A Systematic Review and Meta-analysis", JAMA, 306 (6), 2011, 627-636.
Dhallan, et al., "Methods to Increase the Percentage of Free Fetal DNA Recovered from the Maternal Circulation", JAMA, 291(9), 2004, 1114-1119.
Dhallan, Ravinder et al., "A non-invasive test for prenatal diagnosis based on fetal DNA present in maternal blood: a preliminary study", The Lancet, 369, 2007, 474-481.
Dieffenbach, C W. et al., "General Concepts for PCR Primer Design", PCR Methods Appl.,3, 1993, 30-37.
Ding, C et al., "Direct molecular haplotyping of long-range genomic DNA with M1-PCR", PNAS 100(13), 2003, 7449-7453.
Dohm, J. et al., "Substantial Biases in Ultra-Short Read Data Sets From High-Throughput DNA Sequencing", Nucleic Acids Research, 36 (16), e105, 2008, 10 pgs.
Dolganov, Gregory et al., "A Novel Method of Gene Transcript Profiling in Airway Biopsy Homogenates Reveals Increased Expression of a Na—K+—CI-Cotransporter (NKCC1) in Asthmatic Subjects", Genome Res., 11, 2001, 1473-1483.
Donohoe, Gerard G et al., "Rapid Single-Tube Screening of the C282Y Hemochromatosis Mutation by Real-Time Multiplex Allele-specific PCR without Fluorescent Probes", Clinical Chemistry, 46, 10, 2000, 1540-1547.
Donoso, P. et al., "Current Value of Preimplantation Genetic Aneuploidy Screening in IVF", Human Reproduction Update, 13(1), 2007, 15-25.
Echeverri, et al., "Caffeine's Vascular Mechanisms of Action", International Journal of Vascular Medicine vol. 2010(2010), 10 pages, Aug. 25, 2010.
Ehrich, Mathias et al., "Noninvasive Detection of Fetal Trisomy 21 by Sequencing of DNA in Maternal Blood: A Study in a Clinical Setting", American Journal of Obstetrics & Gynecology, 204, 2011, 205.e1-205.e11.
Eichler, H, "Mild Course of Fetal Rh D Haemolytic Disease due to Maternal Alloimmunisation to Paternal HLA Class I and II Antigens", Vox Sang, 68, 1995, 243-247.

(56) References Cited

OTHER PUBLICATIONS

Ellison, Aaron M., "Bayesian Inference in Ecology", Ecology Letters, 2004, vol. 7, p. 509-520.
Ellonen, P. et al., "Development of SNP Microarray for Supplementary Paternity Testing", International Congress Series,1261, 2004, 12-14.
EP06838311.6, European Communication and Extended European Search Report, mailed Dec. 30, 2008, 8 pgs.
EP08742125.1, European Communication pursuant to Article 94(3) EPC and Examination Report, mailed Feb. 12, 2010, 5 pgs.
Fan, et al., "Whole-genome molecular haplotyping of single cells", Nature Biotechnology, vol. 29, No. 1, Jan. 1, 2011, 51-57.
Fan, Christina H. et al., "Non-Invasive Prenatal Measurement of the Fetal Genome", Nature, doi:10.1038/nature11251, 2012, 26 pgs.
Fan, Christina H et al., "Noninvasive Diagnosis of Fetal Aneuploidy by Shotgun Sequencing DNA from Maternal Blood", PNAS, 105, 42, 2008, 16266-16271.
Fan, Jian-Bing et al., "Highly Parallel Genomic Assay", Nature Reviews, 7, 2006, 632-644.
Fazio, Gennaro et al., "Identification of RAPD Markers Linked to Fusarium Crown and Root Rot Resistance (Frl) in Tomato", Euphytica 105, 1999, 205-210.
Fiorentino, F. et al., "Development and Clinical Application of a Strategy for Preimplantation Genetic Diagnosis of Single Gene Disorders Combined with HLA Matching", Molecular Human Reproduction (Advance Access publication), 10 (6), 2004, 445-460.
Fiorentino, F. et al., "Strategies and Clinical Outcome of 250 Cycles of Preimplantation Genetic Diagnosis for Single Gene Disorders", Human Reproduction, 21, 3, 2006, 670-684.
Fiorentino, Francesco et al., "Short Tandem Repeats Haplotyping of the HLA Region in Preimplantation HLA Matching", European Journal of Human Genetics, 13, 2005, 953-958.
Forejt, et al., "Segmental trisomy of mouse chromosome 17: introducing an alternative model of Down's syndrome", Genomics, 4(6), 2003, 647-652.
Fredriksson, et al., "Multiplex amplification of all coding sequences within 10 cancer genes by Gene-Collector", Nucleic Acids Research, 2007, vol. 35, No. 7 e47, 1-6.
Freeman, Jennifer L. et al., "Copy Number Variation: New Insights in Genome Diversity", Genome Research, 16, 2006, 949-961.
Frost, Mackenzie S et al., "Differential Effects of Chronic Pulsatile Versus Chronic Constant Maternal Hyperglycemia on Fetal Pancreatic B-Cells", Journal of Pregnancy, 2012, Article ID 812094, 2012, 8.
Ganshirt-Ahlert, D. et al., "Ratio of Fetal to Maternal DNA is Less Than 1 in 5000 at different Gestational Ages in Maternal Blood", Clinical Genetics,38, 1990, 38-43.
Ganshirt-Ahlert, D. et al., "Fetal DNA in Uterine Vein Blood", Obstetrics & Gynecology, 80 (4), 1992, 601-603.
Ganshirt-Ahlert, Dorothee et al., "Three Cases of 45,X/46,XYnf Mosaicism", Human Genetics, 76, 1987, 153-156.
Gardina, P. et al., "Ploidy Status and Copy Number Aberrations in Primary Glioblastomas Defined by Integrated Analysis of Allelic Ratios, Signal Ratios and Loss of Heterozygosity Using 500K SNP Mapping Arrays", BMC Genomics, 9 (489), (doi:10.1186/1471-2164-9-489), 2008, 16 pgs.
Ghanta, Sujana et al., "Non-Invasive Prenatal Detection of Trisomy 21 Using Tandem Single Nucleotide Polymorphisms", PLoS One, 5 (10), 2010, 10 pgs.
Gjertson, David W. et al., "Assessing Probability of Paternity and the Product Rule in DNA Systems", Genetica, 96, 1995, 89-98.
Greenwalt, T. et al., "The Quantification of Fetomaternal Hemorrhage by an Enzyme-Linked Antibody Test with Glutaraldehyde Fixation", Vox Sang, 63, 1992, 268-271.
Guerra, J., "Terminal Contributions for Duplex Oligonucleotide Thermodynamic Properties in the Context of Nearest Neighbor Models", Biopolymers, 95(3), (2010), 2011, 194-201.
Guetta, Esther et al., "Analysis of Fetal Blood Cells in the Maternal Circulation: Challenges, Ongoing Efforts, and Potential Solutions", Stem Cells and Development, 13, 2004, 93-99.
Guichoux, et al., "Current Trends in Microsatellite Genotyping", Molecular Ecology Resources, 11, 2011, 591-911.
Hall, M., "Panorama Non-Invasive Prenatal Screening for Microdeletion Syndromes", Apr. 1, 2014 (Apr. 1, 2014), XP055157224, Retrieved from the Internet: URL:http://www.panoramatest.com/sites/default/files/files/PanoramaMicrodeletionsWhite Paper-2.pdf [retrieved on Dec. 8, 2014].
Handyside, et al., "Isothermal whole genome amplification from single and small numbers of cells: a new era for preimplantation genetic diagnosis of inherited disease", Molecular Human Reproduction vol. IO, No. 10 pp. 767-772, 2004.
Hara, Eiji et al., "Subtractive cDNA cloning using oligo(dT)3o-latex and PCR: isolation of cDNA clones specific to undifferentiated human embryonal carcinoma cells", Nucleic Acids Research, 19(25), 1991, 7097-7104.
Hardenbol, P., "Multiplexed Genotyping With Sequence-Tagged Molecular Inversion Probes", Nature Biotechnology, 21 (6), 2003, 673-678.
Hardenbol, Paul et al., "Highly multiplexed molecular inversion probe genotyping: Over 10,000 targeted SNPs genotyped in a singled tube assay", Genome Research, 15, 2005, 269-275.
Harismendy, O et al., "Method for Improving Sequence Coverage Uniformity of Targeted Genomic Intervals Amplified by LR-PCR Using Illumina GA Sequencing-By-Synthesis Technology", Bio Techniques, 46(3), 2009, 229-231.
Harper, J. C. et al., "Recent Advances and Future Developments in PGD", Prenatal Diagnosis, 19, 1999, 1193-1199.
Harton, G.L. et al., "Preimplantation Genetic Testing for Marfan Syndrome", Molecular Human Reproduction, 2 (9), 1996, 713-715.
Hayden, et al., "Multiplex-Ready PCR: A new method for multiplexed SSR and SNP genotyping", BMC Genomics 2008, 9(80), 1-12.
Hellani, A. et al., "Clinical Application of Multiple Displacement Amplification in Preimplantation Genetic Diagnosis", Reproductive BioMedicine Online, 10 (3), 2005, 376-380.
Hellani, Ali et al., "Multiple displacement amplification on single cell and possible PGD applications", Molecular Human Reproduction, 10(11), 2004, 847-852.
Hojsgaard, S. et al., "BIFROST—Block recursive models induced from relevant knowledge, observations, and statistical techniques", Computational Statistics & Data Analysis, 19(2), 1995, 155-175.
Holleley, et al., "Multiplex Manager 1.0: a Cross-Platform Computer Program that Plans and Optimizes Multiplex PCR", BioTechniques, 46, Jun. 2009, 511-517.
Hollox, E. et al., "Extensive Normal Copy Number Variation of a β-Defensin Antimicrobial-Gene Cluster", Am. J. Hum. Genet., 73, 2003, 591-600.
Homer, et al., "Resolving Individuals Contributing Trace Amounts of DNA to Highly Complex Mixtures Using High-Density SNP Genotyping Microarrays", PLOS Genetics, 4 (8), 2008, 9 pgs.
Hoogendoorn, Bastiaan et al., "Genotyping Single Nucleotide Polymorphisms by Primer Extension and High Performance Liquid Chromatography", Hum Genet, 104, 1999, 89-93.
Hospital, F. et al., "A General Algorithm to Compute Multilocus Genotype Frequencies Under Various Mating Systems", vol. 12, No. 6, Jan. 1, 1996, pp. 455-462.
Howie, et al., "Fast and accurate genotype imputation in genome-wide association studies through pre-phasing", Nature Genetics, voi. 44, No. 8, Jul. 22, 2012, 955-959.
Hu, Dong Gui et al., "Aneuploidy Detection in Single Cells Using DNA Array-Based Comparative Genomic Hybridization", Molecular Human Reproduction, 10(4), 2004, 283-289.
Ido, Yasuo et al., "Hyperglycemia-Induced Apoptosis in Human Umbilical Vein Endothelial Cells: Inhibition by the AMP-Activated Protein Kinase Activation", Diabetes, 51, 2002, 159-167.
Illumina Catalog, "Paired-End Sample Preparation Guide, Illumina Catalog# PE-930-1 001, Part# 1005063 Rev. E", 2011, 1-40.
Ishii, et al., "Optimization of Annealing Temperature to Reduce Bias Caused by a Primer Mismatch in Multitemplate PCR", Applied and Environmental Microbiology, Aug. 2001, p. 3753-3755.

(56) References Cited

OTHER PUBLICATIONS

Johnson, D.S. et al., "Comprehensive Analysis of Karyotypic Mosaicism Between Trophectoderm and Inner Cell Mass", Molecular Human Reproduction, 16(12), 2010, 944-949.
Johnson D.S, et al., "Preclinical Validation of a Microarray Method for Full Molecular Karyotyping of Blastomeres in a 24-h Protocol", Human Reproduction, 25 (4), 2010, 1066-1075.
Kaplinski, Lauris et al., "MultiPLX: Automatic Grouping and Evaluation of PCR Primers", Bioinformatics, 21(8), 2005, 1701-1702.
Kazakov, V.I. et al., "Extracellular DNA in the Blood of Pregnant Women", sitologia, 37, 3, 1995, 8.
Kijak, G. et al., "Discrepant Results in the Interpretation of HIV-1 Drug-Resistance Genotypic Data Among Widely Used Algorithms", HIV Medicine, 4, 2003, 72-78.
Konfortov, Bernard A. et al., "An Efficient Method for Multi-Locus Molecular Haplotyping", Nucleic Acids Research, 35 (1), e6, 2007, 8 pgs.
Krjutskov, K. et al., "Development of a single tube 640-plex genotyping method for detection of nucleic acid variations on microarrays", Nucleic Acids Research, vol. 36, No. 12, May 23, 2008, pp. e75-e75.
Kuliev, Anver et al., "Thirteen Years' Experience on Preimplantation Diagnosis: Report of the Fifth International Symposium on Preimplantation Genetics", Reproductive BioMedicine Online, 8, 2, 2004, 229-235.
Lambert-Messerlian, G. et al., "Adjustment of Serum Markers in First Trimester Screening", Journal of Medical Screening, 16 (2), 2009, 102-103.
Lathi, Ruth B. et al., "Informatics Enhanced SNP Microarray Analysis of 30 Miscarriage Samples Compared to Routine Cytogenetics", PLoS One, 7(3), 2012, 5 pgs.
Leary, Rebecca J. et al., "Detection of Chromosomal Alterations in the Circulation of Cancer Patients with Whole-Genome Sequencing", Science Translational Medicine, 4, 162, 2012, 12.
Li, Yind et al., "Non-Invasive Prenatal Diagnosis Using Cell-Free Fetal DNA in Maternal Plasma from PGD Pregnancies", Reproductive BioMedicine Online, 19 (5), 2009, 714-720.
Li, Ying et al., "Size Separation of Circulatory DNA in Maternal Plasma Permits Ready Detection of Fetal DNA Polymorphisms", Clinical Chemistry, 50, 6, 2004, 1002-1011.
Li B., "Highly Multiplexed Amplicon Preparation for Targeted Re-Sequencing of Sample Limited Specimens Using the Ion AmpliSeq Technology and Semiconductor Sequencing", Proceedings of the Annual Meeting of the American Society of Human Genetics [retrieved on Oct. 30, 2012]. Retrieved from the Internet: <URL: http://www.ashg.org/2012meeting/abstracts/fulltext/f120121811.htm>, 2012, 1 pg.
Liao, Gary J.W. et al., "Targeted Massively Parallel Sequencing of Maternal Plasma DNA Permits Efficient and Unbiased Detection of Fetal Alleles", Clinical Chemistry, 57 (1), 2011, 92-101.
Liao, J. et al., "An Alternative Linker-Mediated Polymerase Chain Reaction Method Using a Dideoxynucleotide to Reduce Amplification Background", Analytical Biochemistry 253, 1997, 137-139.
Liew, Michael et al., "Genotyping of Single-Nucleotide Polymorphisms", Clinical Chemistry, 50 (7), 2004, 1156-1164.
Lindroos, Katatina et al., "Genotyping SNPs by Minisequencing Primer Extension Using Oligonucleotide Microarrays", Methods in Molecular Biology, 212, 2003, 149-165.
Lo, et al., "Digital PCR for the Molecular Detection of Fetal Chromosomal Aneuploidy", PNAS, vol. 104, No. 32, 2007, 13116-13121.
Lo, et al., "Fetal Nucleic Acids in Maternal Blood: the Promises", Clin. Chem. Lab. Med., 50 (6), 2012, 995-998.
Lo, et al., "Free Fetal DNA in Maternal Circulation", JAMA, 292 (23), (Letters to the Editor), 2004, 2835-2836.
Lo, "Non-Invasive Prenatal Diagnosis by Massively parallel Sequencing of Maternal Plasma DNA", Open Biol 2: 120086, 2012, 1-5.

Lo, et al., "Prenatal Sex Determination by DNA Amplification from Maternal Peripheral Blood", The Lancet,2, 8676, 1989, 363-1365.
Lo, et al., "Rapid Clearance of Fetal DNA from Maternal Plasma", Am. J. Hum. Genet., 64, 1999, 218-224.
Lo, et al., "Strategies for the Detection of Autosomal Fetal DNA Sequence from Maternal Peripheral Blood", Annals New York Academy of Sciences,731, 1994, 204-213.
Lo, et al., "Two-way cell traffic between mother and fetus: biologic and clinical implications", Blood, 88 (11), 1996, 4390-4395.
Lo, Dennis Y. et al., "Fetal Nucleic Acids in Maternal Plasma: Toward the Development of Noninvasive Prenatal Diagnosis of Fetal Chromosomal Aneuploidies", Ann. N.Y. Acad. Sci., 1137, 2008, 140-143.
Lo, Dennis Y. et al., "Plasma placental RNA allelic ratio permits noninvasive prenatal chromosomal aneuploidy detection", Nature Medicine, 13(2), 2007, 218-223.
Lo, Dennis Y.M. et al., "Maternal Plasma DNA Sequencing Reveals the Genome-Wide Genetic and Mutational Profile of the Fetus", Science Translational Medicine, 2, 61, 2010, 13.
Lo, Dennis Y.M. et al., "Presence of Fetal DNA in Maternal Plasma and Serum", The Lancet, 350, 1997, 485-487.
Lo, Dennis Y.M. et al., "Quantitative Analysis of Fetal DNA in Maternal Plasma and Serum: Implications for Noninvasive Prenatal Diagnosis", Am. J. Hum. Genet., 62, 1998, 768-775.
Lo, Y. M. D. et al., "Prenatal Determination of Fetal Rhesus D Status by DNA Amplification of Peripheral Blood of Rhesus-Negative Mothers", Annals New York Academy of Sciences, 731, 1994, 229-236.
Lo, Y. M. D. et al., "Prenatal Determination of Fetal RhD Status by Analysis of Peripheral Blood of Rhesus Negative Mothers", The Lancet, 341, 1993, 1147-1148.
Lo, Y. M. D. et al., "Detection of Single-Copy Fetal DNA Sequence from Maternal Blood", The Lancet, 335, 1990, 1463-1464.
Lo, Y. et al., "Detection of Fetal RhD Sequence from Peripheral Blood of Sensitized RhD-Negative Pregnant Women", British Journal of Haematology, 87, 1994, 658-660.
Lun, Fiona M. et al., "Noninvasive Prenatal Diagnosis of Monogenic Diseases by Digital Size Selection and Relative Mutation Dosage on DNA in Maternal Plasma", PNAS, 105(50), 2008, 19920-19925.
Maniatis, T. et al., "In: Molecular Cloning: A Laboratory Manual", Cold Spring Harbor Laboratory, New York, Thirteenth Printing, 1986, 458-459.
Mansfield, Elaine S., "Diagnosis of Down Syndrome and Other Aneuploidies Using Quantitative Polymerase Chain Reaction and Small Tandem Repeat Polymorphisms", Human Molecular Genetics, 2, 1, 1993, 43-50.
Markoulatos, P. et al., "Multiplex Polymerase Chain Reaction: A Practical Approach", Journal of Clinical Laboratory Analysis, 16, 2002, 47-51.
May, Rober M. et al., "How Many Species Are There on Earth?", Science, 241, 1988, 1441-1449.
McCray, Alexa T. et al., "Aggregating UMLS Semantic Types for Reducing Conceptual Complexity", MEDINFO 2001: Proceedings of the 10th World Congress on Medical Informatics (Studies in Health Technology and Informatics, 84, V. Patel et al. (eds.), IOS Press Amsterdam, 2001, 216-220.
Mennuti, M. et al., "Is It Time to Sound an Alarm About False-Positive Cell-Free DNA Testing for Fetal Aneuploidy?", American Journal of Obstetrics, 2013, 5 pgs.
Mersy, et al., "Noninvasive Detection of Fetal Trisomy 21: Systematic Review and Report of Quality and Outcomes of Diagnostic Accuracy Studies Performed Between 1997 and 2012", Human Reproduction Update, 19 (4), 2013, 318-329.
Miller, Robert, "Hyperglycemia-Induced Changes in Hepatic Membrane Fatty Acid Composition Correlate with Increased Caspase-3 Activities and Reduced Chick Embryo Viability", Comparative Biochemistry and Physiology, Part B, 141, 2005, 323-330.
Miller, Robert R., "Homocysteine-Induced Changes in Brain Membrane Composition Correlate with Increased Brain Caspase-3 Activities and Reduced Chick Embryo Viability", Comparative Biochemistry and Physiology Part B, 136, 2003, 521-532.

(56) References Cited

OTHER PUBLICATIONS

Morand, et al., "Hesperidin contributes to the vascular protective effects of orange juice: a randomized crossover study in healthy volunteers", Am J Clin Nutr. 2011, 93 (1), 73-80, Epub Nov. 10, 2010.
Munne, S. et al., "Chromosome abnormalities in human embryos", Human Reproduction update, 4 (6), 842-855.
Murtaza, M. et al., "Non-Invasive Analysis of Acquired Resistance to Cancer Therapy by Sequencing of Plasma DNA", Nature, 2013, 6 pgs.
Muse, Spencer V., "Examining rates and patterns of nucleotide substitution in plants", Plant Molecular Biology 42, 2000, 25-43.
Myers, Chad L. et al., "Accurate Detection of Aneuploidies in Array CGH and Gene Expression Microarray Data", Bioinformatics, 20 (18), 2004, 3533-3543.
Nannya, Yasuhito et al., "A Robust Algorithm for Copy Number Detection Using High-density Oligonucleotide Single Nucleotide Polymorphism Genotyping Arrays", Cancer Res., 65, 14, 2005, 6071-6079.
Nicolaides, K. et al., "Noninvasive Prenatal Testing for Fetal Trisomies in a Routinely Screened First-Trimester Population", American Journal of Obstetrics (article in press), 207, 2012, 1.e1-1.e6.
Nicolaides, K.H et al., "Validation of Targeted Sequencing of Single-Nucleotide Polymorphisms for Non-Invasive Prenatal Detection of Aneuploidy of Chromosomes 13, 18, 21, X, and Y", Prenatal Diagnosis, 33, 2013, 575-579.
Nicolaides, Kypros H. et al., "Prenatal Detection of Fetal Triploidy from Cell-Free DNA Testing in Maternal Blood", Fetal Diagnosis and Therapy, 2013, 1-6.
Nygren, et al., "Quantification of Fetal DNA by Use of Methylation-Based DNA Discrimination", Clinical Chemistry, 56:10, 2010, 1627-1635.
Ogino, S. et al., "Bayesian Analysis and Risk Assessment in Genetic Counseling and Testing", Journal of Molecular Diagnostics, 6 (1), 2004, 9 pgs.
O'Malley, R et al., "An adapter ligation-mediated PCR method for high-throughput mapping of T-DNA inserts in the Arabidopsis genome", Nat. Protoc. 2, 2007, 2910-2917.
Orozco A.F., et al., "Placental Release of Distinct DNA-Associated Micro-Particles into Maternal Circulation: Reflective of Gestation Time and Preeclampsia", Placenta, 30, 2009, 891-897.
Ozawa, Makiko et al., "Two Families with Fukuyama Congenital Muscular Dystrophy that Underwent in Utero Diagnosis Based on Polymorphism Analysis", Clinical Muscular Dystrophy: Research in Immunology and Genetic Counseling—FY 1994 Research Report, (including text in Japanese), 1994, 8.
Paez, Guillermo J. et al., "Genome coverage and sequence fidelity of Φ29 polymerase-based multiple strand displacement whole genome amplification", Nucleic Acids Research, 32 (9), 2004, 1-11.
Page, S. L. et al., "Chromosome Choreography: The Meiotic Ballet", Science, 301, 2003, 785-789.
Palomaki, Glenn et al., "DNA Sequencing of Maternal Plasma Reliably Identifies Trisomy 18 and Trisomy 13 as Well as Down Syndrome: an International Collaborative Study", Genetics in Medicine, 2012, 10.
Palomaki, Glenn E. et al., "DNA Sequencing of Maternal Plasma to Detect Down Syndrome: An International Clinical Validation Study", Genetics in Medicine (pre-print version), 13, 2011, 8 pgs.
Papageorgiou, Elisavet A. et al., "Fetal-Specific DNA Methylation Ratio Permits Noninvasive Prenatal Diagnosis of Trisomy 21", Nature Medicine (advance online publication),17, 2011, 5 pgs.
PCT/US2006/045281, International Preliminary Report on Patentability, mailed May 27, 2008, 1 pg.
PCT/US2006/045281, International Search Report and Written Opinion, mailed Sep. 28, 2007, 7 pgs.
PCT/US2008/003547, International Search Report, mailed Apr. 15, 2009, 5 pgs.
PCT/US2009/034506, International Search Report, mailed Jul. 8, 2009, 2 pgs.
PCT/US2009/045335, International Search Report, mailed Jul. 27, 2009, 1 pg.
PCT/US2009/052730, International Search Report, mailed Sep. 28, 2009, 1 pg.
PCT/US2010/050824, International Search Report, mailed Nov. 15, 2010, 2 pgs.
PCT/US2011/037018, International Search Report, mailed Sep. 27, 2011, 2 pgs.
PCT/US2011/061506, International Search Report, mailed Mar. 16, 2012, 1 pgs.
PCT/US2011/066938, International Search Report, mailed Jun. 20, 2012, 1 pg.
PCT/US2012066339, International Search Report, mailed Mar. 5, 2013, 1 pg.
PCT/US2013/028378, International Search Report and Written Opinion, mailed May 28, 2013, 11 pgs.
PCT/US2013/57924, International Search Report and Written Opinion, mailed Feb. 18, 2014, 8 pgs.
PCT/US2014/051926, International Search Report and Written Opinion, mailed Dec. 9, 2014, 8 pgs.
Pena, Sergio D.J. et al., "Paternity Testing in the DNA Era", Trends in Genetics, 10, 6, 1994, 204-209.
Perkel, Jeffrey M., "Overcoming the Challenges of Multiplex PCR", Biocompare Editorial Article, 2012, 1-5.
Perry, George H. et al., "The Fine-Scale and Complex Architecture of Human Copy-Number Variation", The American Journal of Human Genetics,82, 2008, 685-695.
Pertl, B. et al., "Detection of Male and Female Fetal DNA in Maternal Plasma by Multiplex Fluorescent Polymerase Chain Reaction Amplification of Short Tandem Repeats", Hum. Genet., 106, 2000, 45-49.
Peters, David P. et al., "Noninvasive Prenatal Diagnosis of a Fetal Microdeletion Syndrome", New England Journal of Medicine, 365 (19), 2011, 1847-1848.
Pfaffl, Michael W., "Relative Expression Software Tool (REST ©) for Group-Wise Comparison and Statistical Analysis of Relative Expression Results in real-Time PCR", Nucleic Acids Research, 30 (9), 2002, 10 pgs.
Phillips, C. et al., "Resolving Relationship Tests that Show Ambiguous STR Results Using Autosomal SNPs as Supplementary Markers", Forensic Science International: Genetics 2, 2008, 198-204.
Podder, Mohua et al., "Robust SN P genotyping by multiplex PCR and arrayed primer", BMC Medical Genomics,1 (5), 2008, 1-15.
Porreca, Gregory J. et al., "Multiplex Amplification of Large Sets of Human Exons", Nature Methods, 4, (advance online publication), 2007, 6.
Price, T.S. et al., "SW-Array: a dynamic programming solution for the identification of copy-number changes in genomic DNA using array comparative genome hybridization data", Nucleic Acids Research, vol. 33, No. 11, Jun. 16, 2005, pp. 3455-3464.
Rabinowitz, et al., "Accurate Prediction of HIV-1 Drug Response from the Reverse Transcriptase and Protease Amino Acid Sequences Using Sparse Models Created by Convex Optimization", Bioinformatics, 22, 5, 2006, 541-549.
Rabinowitz, Matthew et al., "Origins and rates of aneuploidy inhuman blastomeres", Fertility and Sterlity, 97 (2), 2012, 395-401.
Rabinowitz, Matthew. et al., "Non-Invasive Prenatal Aneuploidy Testing of Chromosomes 13, 18, 21, X, and Y Using Targeted Sequencing of Polymorphic Loci", The American Society of Human Genetics, meeting poster, 2012, 1 pg.
Rahmann, Sven et al., "Mean and variance of the Gibbs free energy of oligonucleotides in the nearest neighbor model under varying conditions", Bioinformatics, 20 (17), 2004, 2928-2933.
Rava, Richard P. et al., "Circulating Fetal Cell-Free DNA Fraction Differ in Autosomal Aneuploidies and Monosomy X", Clinical Chemistry, 60 (1), 2013, 8 pgs.
Rechitsky, Svetlana et al., "Preimplantation Genetic Diagnosis with HLA Matching", Reproductive Bio Medicine Online, 9, 2, 2004, 210-221.
Renwick, Pamela et al., "Proof of Principle and First Cases Using Preimplantation Genetic Haplotyping—A Paradigm Shift for Embryo Diagnosis", Reproductive BioMedicine Online, 13 (1), 2006, 110-119.

(56) References Cited

OTHER PUBLICATIONS

Ricciotti, Hope, "Eating by Trimester", Online. Retrieved from Internet:<http://www.youandyourfamily.com/article.php?story=Eating+by+Trimester>, 2014, 3.
Roper, Stephen M. et al., "Forensic Aspects of DNA-Based Human Identity Testing", Journal of Forensic Nursing, 4, 2008, 150-156.
Roux, K H., "Optimization and troubleshooting in PCR", Genome Research, PCR Methods and Applications, vol. 4, 1995, 185-194.
Rozen, Steve et al., "Primer3 on the WWW for General Users and for Biologis Programmers", Methods in Molecular Biology, 132: Bioinformatics Methods and Protocols, 1999, 365-386.
Russell, L M., "X Chromosome Loss and Ageing", Cytogenetic and Genome Res., 116, 2007, 181-185.
Ryan, et al., "The importance of phase information for human genomics", Nature Reviews Genetics, vol. 12, No. 3, Mar. 1, 2011.
Ryan, Allison et al., "Informatics-Based, Highly Accurate, Noninvasive Prenatal Paternity Testing", Genetics in Medicine (advance online publication), 2012, 5 pgs.
Rychlik, et al., "Optimization of the annealing temperature for DNA amplification in vitro", Nuceic Acids Research, 18 (21), 1990, 6409-6412.
Samango-Sprouse, C. et al., "SNP-Based Non-Invasive Prenatal Testing Detects Sex Chromosome Aneuploidies with High Accuracy", Prenatal Diagnosis, 33, 2013, 1-7.
Sander, Chris, "Genetic Medicine and the Future of Health Care", Science, 287 (5460), 2000, 1977-1978.
Santalucia, J. et al., "The Thermodynamics of DNA Structural Motifs", Annu. Rev. Biophys. Biomol. Struct., 33, 2004, 415-440.
Santalucia, John J.R. et al., "Improved Nearest-Neighbor Parameters for Predicting DNA Duplex Stability", Biochemistry, 35, 1996, 3555-3562.
Sasabe, Yutaka, "Genetic Diagnosis of Gametes and Embryos Resulting from ART", Japanese Journal of Fertility and Sterility, 2001, vol. 46, No. 1, p. 43-46.
Schoumans, J. et al., "Detection of chromosomal imbalances in children with idiopathic mental retardation by array based comparative genomic hybridisation (array-CGH)", JMed Genet, 42, 2005, 699-705.
Sebat, Jonathan et al., "Strong Association of De Novo Copy Number Mutations with Autism", Science, 316, 2007, 445-449.
Sehnert, A. et al., "Optimal Detection of Fetal Chromosomal Abnormalities by Massively Parallel DNA Sequencing of Cell-Free Fetal DNA from Maternal Blood", Clinical Chemistry (papers in press), 57 (7), 2011, 8 pgs.
Sermon, Karen et al., "Preimplantation genetic diagnosis", The Lancet, Lancet Limited, 363 (9421), 2000, 1633-1641.
Servin, B. et al., "MOM: A Program to Compute Fully Informative Genotype Frequencies in Complex Breeding Schemes", Journal of Heredity, vol. 93, No. 3, Jan. 1, 2002, pp. 227-228.
Shaw-Smith, et al., "Microarray Based Comparative Genomic Hybridisation (array-CGH) Detects Submicroscopic Chromosomal Deletions and Duplications in Patients with Learning Disability/ Mental Retardation and Dysmorphic Features", J. Med. Genet., 41, 2004, 241-248.
Shen, et al., "High-quality DNA sequence capture of 524 disease candidate genes", High-quality DNA sequence capture of 524 disease candidate genes, Proceedings of the National Academy of Sciences, vol. 108, No. 16, Apr. 2011, pp. 6549-6554.
Shen, Zhiyong, "MPprimer: a program for reliable multiplex PCR primer design", BMC Bioinformatics 2010, 11:143, 1-7.
Sherlock, J. et al., "Assessment of Diagnostic Quantitative Fluorescent Multiplex Polymerase Chain Reaction Assays Performed on Single Cells", Annals of Human Genetics, 62, 1, 1998, 9-23.
Simpson, J. et al., "Fetal Cells in Maternal Blood: Overview and Historical Perspective", Annals New York Academy of Sciences, 731, 1994, 1-8.
Sint, Daniela et al., "Advances in Multiplex PCR: Balaning Primer Efficiencies and Improving Detection Success", Methods in Ecology and Evolution, 3, 2012, 898-905.

Slater, Howard et al., "High-Resolution Identification of Chromosomal Abnormalities Using Oligonucleotide Arrays Containing 116,204 SNPs", Am. J. Hum. Genet., 77, 5, 2005, 709-726.
Snijders, Antoine et al., "Assembly of Microarrays for Genome-Wide Measurement of DNA Copy Number", Nature Genetic, 29, 2001, 263-264.
Sparks, A. et al., "Non-Invasive Prenatal Detection and Selective Analysis of Cell-Free DNA Obtained from Maternal Blood: Evaluation for Trisomy 21 and Trisomy 18", American Journal of Obstetrics & Gynecology 206, 2012, 319.e1-319.e9.
Sparks, Andrew B. et al., "Selective Analysis of Cell-Free DNA in Maternal Blood for Evaluation of Fetal Trisomy", Prenatal Diagnosis, 32, 2012, 1-7.
Spiro, Alexander et al., "A Bead-Based Method for Multiplexed Identification and Quantitation of DNASequences Using Flow Cytometry", Applied and Environmental Microbiology, 66, 10, 2000, 4258-4265.
Spits, C. et al., "Optimization and Evaluation of Single-Cell Whole Genome Multiple Displacement Amplification", Human Mutation, 27 (5), 2006, 496-503.
Srinivasan, et al., "Noninvasive Detection of Fetal Subchromosome Abnormalities via Deep Sequencing of Maternal Plasma", The American Journal of Human Genetics, 92, Feb. 2013, 167-176.
Stephens, Mathews et al., "A Comparison of Bayesian Methods for Haplotype Reconstruction from Population Genotype Data", Am. J. Hum. Genet., 73, 2003, 1162-1169.
Stevens, Robert et al., "Ontology-Based Knowledge Representation for Bioinformatics", Briefings in Bioinformatics, 1, 4, 2000, 398-414.
Steyerberg, E.W. et al., "Application of Shrinkage Techniques in Logistic Regression Analysis: A Case Study", Statistica Neerlandica, 55 (1), 2001, 76-88.
Strom, C. et al., "Three births after preimplantation genetic diagnosis for cystic fibrosis with sequential first and second polar body analysis", American Journal of Obstetrics and Gynecology, 178 (6), 1998, 1298-1306.
Strom, Charles M. et al., "Neonatal Outcome of Preimplantation Genetic Diagnosis by Polar Body Removal: The First 109 Infants", Pediatrics, 106(4), 2000, 650-653.
Stroun, Maurice et al., "Prehistory of the Notion of Circulating Nucleic Acids in Plasma/Serum (CNAPS): Birth of a Hypothesis", Ann. N.Y. Acad. Sci., 1075, 2006, 10-20.
Su, S.Y. et al., "Inferring combined CNV/SNP haplotypes from genotype data", Bioinformatics, vol. 26, No. 11, 1, 2010, 1437-1445.
Sun, Guihua et al., "SNPs in human miRNA genes affect biogenesis and function", RNA, 15(9), 2009, 1640-1651.
Sweet-Kind Singer, J. A. et al., "Log-penalized linear regression", IEEE International Symposium on Information Theory Proceedings, 2003, 286.
Tamura, et al., "Sibling Incest and formulation of paternity probability: case report", Legal Medicine, 2000, vol. 2, 189-196.
Tang, et al., "Multiplex fluorescent PCR for noninvasive prenatal detection of fetal-derived paternally inherited diseases using circulatory fetal DNA in maternal plasma", Eur J Obstet Gynecol Reprod Biol, 2009, v.144, No. 1, p. 35-39.
Tang, N. et al., "Detection of Fetal-Derived Paternally Inherited X-Chromosome Polymorphisms in Maternal Plasma", Clinical Chemistry, 45 (11), 1999, 2033-2035.
Thomas, M.R. et al., "The Time of Appearance and Disappearance of Fetal DNA from the Maternal Circulation", Prenatal Diagnosis, 15, 1995, 641-646.
Tong, Yu et al., "Noninvasive Prenatal Detection of Fetal Trisomy 18 by Epigenetic Allelic Ratio Analysis in Maternal Plasma: Theoretical and Empirical Considerations", Clinical Chemistry, 52 (12), 2006, 2194-2202.
Tong, Yu K. et al., "Noninvasive Prenatal Detection of Trisomy 21 by Epigenetic-Genetic Chromosome-Dosage Approach", Clinical Chemistry, 56 (1), 2010, 90-98.
Troyanskaya, Olga G. et al., "A Bayesian Framework for Combining Heterogeneous Data Sources for Gene Function Prediction (in *Saccharomyces cerevisiae*)", PNAS, 100(14), 2003, 8348-8353.

(56) References Cited

OTHER PUBLICATIONS

Tsui, Nancy B.Y. et al., "Non-Invasive Prenatal Detection of Fetal Trisomy 18 by RNA-SNP Allelic Ratio Analysis Using Maternal Plasma SERPINB2 mRNA: A Feasibility Study", Prenatal Diagnosis, 29, 2009, 1031-1037.
Turner, E. et al., "Massively Parallel Exon Capture and Library-Free Resequencing Across 16 Genomes", Nature Methods, 6 (5), 2009, 315-316.
Vallone, Peter, "AutoDimer: a Screening Tool for Primer-Dimer and Hairpin Structures", Bio Techniques, 37, 2004, 226-231.
Varley, Katherine Elena et al., "Nested Patch PCR Enables Highly Multiplexed Mutation Discovery in Candidate Genes", Genome Res., 18 (11), 2008, 1844-1850.
Verlinsky, Y. et al., "Over a Decade of Experience with Preimplantation Genetic Diagnosis", Fertility and Sterility, 82 (2), 2004, 302-303.
Wagner, Jasenka et al., "Non-Invasive Prenatal Paternity Testing from Maternal Blood", Int. J. Legal Med., 123, 2009, 75-79.
Wang, Eric et al., "Gestational Age and Maternal Weight Effects on Fetal Cell-Free DNA in Maternal Plasma", Prenatal Diagnosis, 33, 2013, 662-666.
Wang, Hui-Yun et al., "A genotyping system capable of simultaneously analyzing >1000 single nucleotide polymorphisms in a haploid genome", Genome Res., 15, 2005, 276-283.
Wang, Yuker et al., "Allele quantification using molecular inversion probes (MIP)", Nucleic Acids Research, vol. 33, No. 21, 2005, 14 pgs.
Wapner, R. et al., "Chromosomal Microarray Versus Karyotyping for Prenatal Diagnosis", The New England Journal of Medicine, 367 (23), 2012, 2175-2184.
Watkins, N. et al., "Thermodynamic contributions of single internal rA •dA, rC • dC, rG • dG and rU • dT mismatches in RNA/DNA duplexes", Nucleic Acids Research, 9 (5), 2010, 1894-1902.
Wells, D., "Microarray for Analysis and Diagnosis of Human Embryos", 12th International Congress on Prenatal Diagnosis and Therapy, Budapest, Hungary, 2004, 9-17.
Wells, Dagan, "Advances in Preimplantation Genetic Diagnosis", European Journal of Obstetrics and Gynecology and Reproductive Biology, 115S, 2004, S97-S101.
Wells, Dagan, "Detailed Chromosomal and Molecular Genetic Analysis of Single Cells by Whole Genome Amplification and Comparative Genomic Hybridisation", Nucleic Acids Research, 27, 4, 1999, 1214-1218.
Wen, Daxing et al., "Universal Multiples PCR: A Novel Method of Simultaneous Amplification of Multiple DNA Fragments", Plant Methods, 8 (32), 2012, 1-9.
Wilton, et al., "Birth of a Healthy Infant After Preimplantation Confirmation of Euploidy by Comparative Genomic Hybridization", N. Engl. J. Med., 345 (21), 2001, 1537-1541.
Wilton, L., "Preimplantation Genetic Diagnosis and Chromosome Analysis of Blastomeres Using Comparative Genomic Hybridization", Human Reproduction Update, 11 (1), 2005, 33-41.
Xia, Tianbing et al., "Thermodynamic Parameters for an Expanded Nearest-Neighbor Model for Formation of RNA Duplexes with Watson-Crick Base Pairs", Biochemistry, 37, 1998, 14719-14735.
Yeh, Iwei et al., "Knowledge Acquisition, Consistency Checking and Concurrency Control for Gene Ontology (GO)", Bioinformatics, 19, 2, 2003, 241-248.
You, Frank M. et al., "BatchPrimer3: A high throughput web application for PCR and sequencing primer design", BMC Bioinformatics, Biomed Central, London, GB, vol. 9, No. 1, 2008, p. 253.
Zhang, Rui et al., "Quantifying RNA allelic ratios by microfluidic multiplex PCR and sequencing", Nature Methods, 11 (1), 2014, 51-56.
Zhao, Xiaojun et al., "An Integrated View of Copy Number and Allelic Alterations in the Cancer Genome Using Single Nucleotide Polymorphism Arrays", Cancer Research, 64, 2004, 3060-3071.
Zhou, W. et al., "Counting Alleles Reveals a Connection Between Chromosome 18q Loss and Vascular Invasion", Nature Biotechnology, 19, 2001, 78-81.
Zimmermann, et al., "Noninvasive Prenatal Aneuploidy Testing of Chromosomes 13, 18, 21 X, and Y, Using targeted Sequencing of Polymorphic Loci", Prenatal Diagnosis, 32, 2012, 1-9.
Chakraborty, R. et al., "Paternity Exclusion by DNA Markers: Effects of Paternal Mutations", Journal of Forensic Sciences, vol. 41, No. 4, Jul. 1996, 671-677.
Pearson, K., "On the criterion that a given system of deviations from the probable in the case of a correlated system of variables is such that it can be reasonably supposed to have arisen from random sampling", Philosophical Magazine Series 5, vol. 50, Issue 302, 1900, 157-175.

* cited by examiner

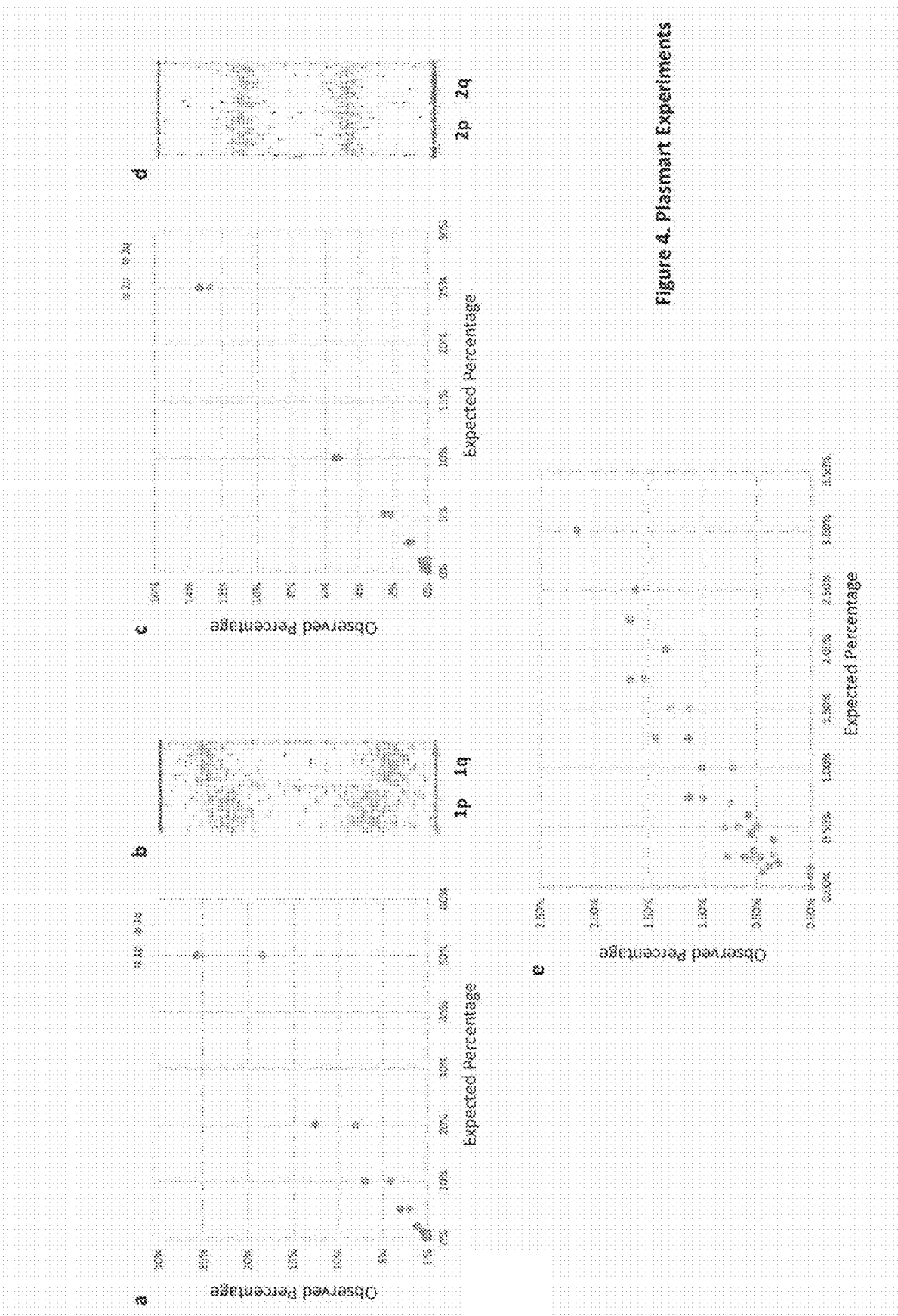
Figure 4. Plasmart Experiments

CELL FREE DNA DIAGNOSTIC TESTING STANDARDS

FIELD OF THE INVENTION

The invention is in the field of nucleic acid-based diagnostics

BACKGROUND

Cell free DNA found in the blood and other bodily tissues can be used to detect and diagnose many genetic disorders. Numerous methods exist for non-invasive prenatal genetic diagnostics. Non-invasive prenatal genetic diagnoses can be performed on cell-free DNA, e.g., obtained from blood, from a patient. Cell-free DNA can also be used to detect or monitor the presence of tumor cells in patient. Such methods are complex to carry out and are subject to numerous errors resulting in imprecision and inaccuracy. It is important for commercial laboratories to demonstrate proficiency in testing in order to obtain regulatory approval for carrying out such tests. Accordingly, it is necessary for laboratories carrying out such procedures to engage in proficiency testing using standards for analysis. Such standard testing can be problematic given the relative scarcity of naturally occurring samples and the variability between such samples. Provided herein are methods and compositions for addressing this problem.

SUMMARY

Provided below is a non-exhaustive list of some embodiments of the invention.

An embodiment of the invention is a prenatal nucleic acid proficiency testing standard composition, comprising a first nucleosomal nucleic acid preparation derived from a first cell source and a second nucleosomal nucleic acid preparation from a second cell source, wherein the quantity of the first nucleic acid preparation is greater than the quantity of the second nucleic acid preparation. In another embodiment, the invention is a prenatal nucleic acid proficiency testing standard composition, comprising a first nucleosomal nucleic acid preparation derived from a first cell source and a second nucleosomal nucleic acid preparation from a second cell source, wherein the quantity of the first nucleic acid preparation is approximately equal to the quantity of the second nucleic acid preparation.

In some embodiments the prenatal nucleic acid proficiency testing standard composition, the first nucleosomal nucleic acid preparation is derived from a primary cell source. In some embodiments the first nucleosomal nucleic acid preparation is derived from a cell line. In some embodiments the first cell source and the second cell source are cell lines. In some embodiments the first cell source and the second cell source are primary cell sources. In some embodiments primary cell source is blood cells from a buffy coat layer.

In some embodiments of the subject compositions nucleosomal nucleic acid preparation has been prepared with an endonuclease. The endonuclease can be a micrococcal endonuclease. In some embodiments the first nucleosomal nucleic acid preparation and the second nucleosomal nucleic acid are one or more nucleosomal ladder components. In some embodiments the first nucleosomal nucleic acid preparation and the second nucleosomal nucleic acid comprise a mononucleosomal ladder fraction. In some embodiments the first nucleosomal nucleic acid preparation comprises a dinucleosomal ladder fraction. In some embodiments the first nucleosomal nucleic acid preparation comprises a trinucleosomal ladder fraction. In some embodiments, the second nucleosomal nucleic acid preparation comprises a dinucleosomal ladder fraction. In some embodiments the second nucleosomal nucleic acid preparation comprises a trinucleosomal ladder fraction. In some embodiments, second nucleosomal nucleic acid preparation comprises a dinucleosomal ladder fraction. In some embodiments the second nucleosomal nucleic acid preparation comprises a trinucleosomal ladder fraction.

In some embodiments the amount of the second nucleosomal nucleic acid preparation is less than 40% of the total nucleic acid in the composition. In some embodiments the amount of the second nucleosomal nucleic acid preparation is less than 30% of the total nucleic acid in the composition. In some embodiments the second nucleosomal nucleic acid preparation is less than 20% of the total nucleic acid in the composition. In some embodiments the amount of the second nucleosomal nucleic acid preparation is less than 10% of the total nucleic acid in the composition.

The first cell source and the second cell source may be from genetically related individuals, including embodiments for use in the analysis of fetal DNA. In some embodiments the first cell source is the mother of the second cell source. In some embodiments the first cell source is the father of the second cell source. In some embodiments the first cell source is a sibling of the second cell source.

An embodiment of the invention is a composition that cancer cell nucleic acid proficiency testing standard for diagnostics that detect cell free cancer DNA, comprising a first nucleosomal nucleic acid preparation derived from a first cell source and a second nucleosomal nucleic acid preparation from a second cell source, wherein the quantity of the first nucleic acid preparation is greater than the quantity of the second nucleic acid preparation. In another embodiment, the invention is a prenatal nucleic acid proficiency testing standard composition, comprising a first nucleosomal nucleic acid preparation derived from a first cell source and a second nucleosomal nucleic acid preparation from a second cell source, wherein the quantity of the first nucleic acid preparation is approximately equal to the quantity of the second nucleic acid preparation. In some embodiments the cancer cell nucleic acid proficiency testing standard composition comprises a first nucleosomal nucleic acid preparation that is derived from a primary cell source. In some embodiments the first nucleosomal nucleic acid preparation is derived from a cell line. In some embodiments the first cell source and the second cell source are cell lines. In some embodiments the first cell source and the second cell source are primary cell sources.

In some embodiments of the subject compositions, nucleosomal nucleic acid preparation can be been prepared with an endonuclease. The endonuclease can be a micrococcal endonuclease. In some embodiments the first nucleosomal nucleic acid preparation and the second nucleosomal nucleic acid are nucleosomal ladder fractions. In some embodiments the first nucleosomal nucleic acid preparation and the second nucleosomal nucleic acid comprise mononucleosomal ladder fractions. In some embodiments the first nucleosomal nucleic acid preparation comprises a dinucleosomal ladder fraction. In some embodiments the first nucleosomal nucleic acid preparation comprises a trinucleosomal ladder fraction. In some embodiments, the second nucleosomal nucleic acid preparation comprises a dinucleosomal ladder fraction. In some embodiments the second nucleosomal nucleic acid preparation comprises trinucleosomal ladder fractions. In some embodiments, second nucleosomal nucleic acid preparation comprises dinucleosomal ladder fractions. In some embodiments the second nucleosomal nucleic acid preparation comprises trinucleosomal ladder fractions.

In some embodiments the amount of the second nucleosomal nucleic acid preparation is less than 40% of the total nucleic acid in the composition. In some embodiments the amount of the second nucleosomal nucleic acid preparation is less than 30% of the total nucleic acid in the composition. In some embodiments the second nucleosomal nucleic acid preparation is less than 20% of the total nucleic acid in the composition. In some embodiments the amount of the second nucleosomal nucleic acid preparation is less than 10% of the total nucleic acid in the composition.

The first cell source and the second cell source may be from genetically related individuals from the same individual, or from genetically unrelated individuals. In some embodiments the first cell source is the mother of the second cell source. In some embodiments the first cell source is non-cancerous tissue and the second cell source is a corresponding cancer cell culture.

The invention also includes sets of the subject cell free DNA diagnostic testing standards, wherein the set comprise at least two cell free DNA diagnostic testing standards. In some embodiments, the sets can comprise cell free DNA diagnostic testing standards that are the same as one another with respect to the identity of the cell sources, but differ with respect to one another with respect to the ratios of the different nucleosomal nucleic acid components of the mixture.

The invention also includes methods of making the subject prenatal nucleic acid proficiency testing standard compositions and nucleic acid proficiency testing standard compositions made by the methods. Embodiments of such methods include mixing a first nucleosomal nucleic acid preparation derived from a first cell source, and a second nucleosomal nucleic acid preparation from a second cell source, wherein the quantity of the first nucleic acid preparation is greater than the quantity of the second nucleic acid preparation. Embodiments of the subject methods include methods of making all of the compositions described herein.

The invention also includes methods of making the subject cell-free nucleic acid diagnostic proficiency testing standard compositions prepared by the subject methods. Embodiments of such methods include mixing a first nucleosomal nucleic acid preparation derived from a first cell source, and a second nucleosomal nucleic acid preparation from a second cell source, wherein the quantity of the first nucleic acid preparation is greater than (or in some embodiment, equal to) the quantity of the second nucleic acid preparation. Embodiments of the subject methods include methods of making all of the compositions described herein. The cell-free nucleic acid diagnostic proficiency testing standard compositions prepared by the subject methods can be used for testing proficiency to perform diagnosis or detection of a wide range of genetic disorders such as cancer or fetal chromosomal abnormalities.

BRIEF DESCRIPTION OF THE DRAWINGS

FIGS. 4a-4e show the detection of copy number variants in cell-free DNA diagnostics standards, (Plasmart).

DETAILED DESCRIPTION OF SPECIFIC EMBODIMENTS

Figure 1:
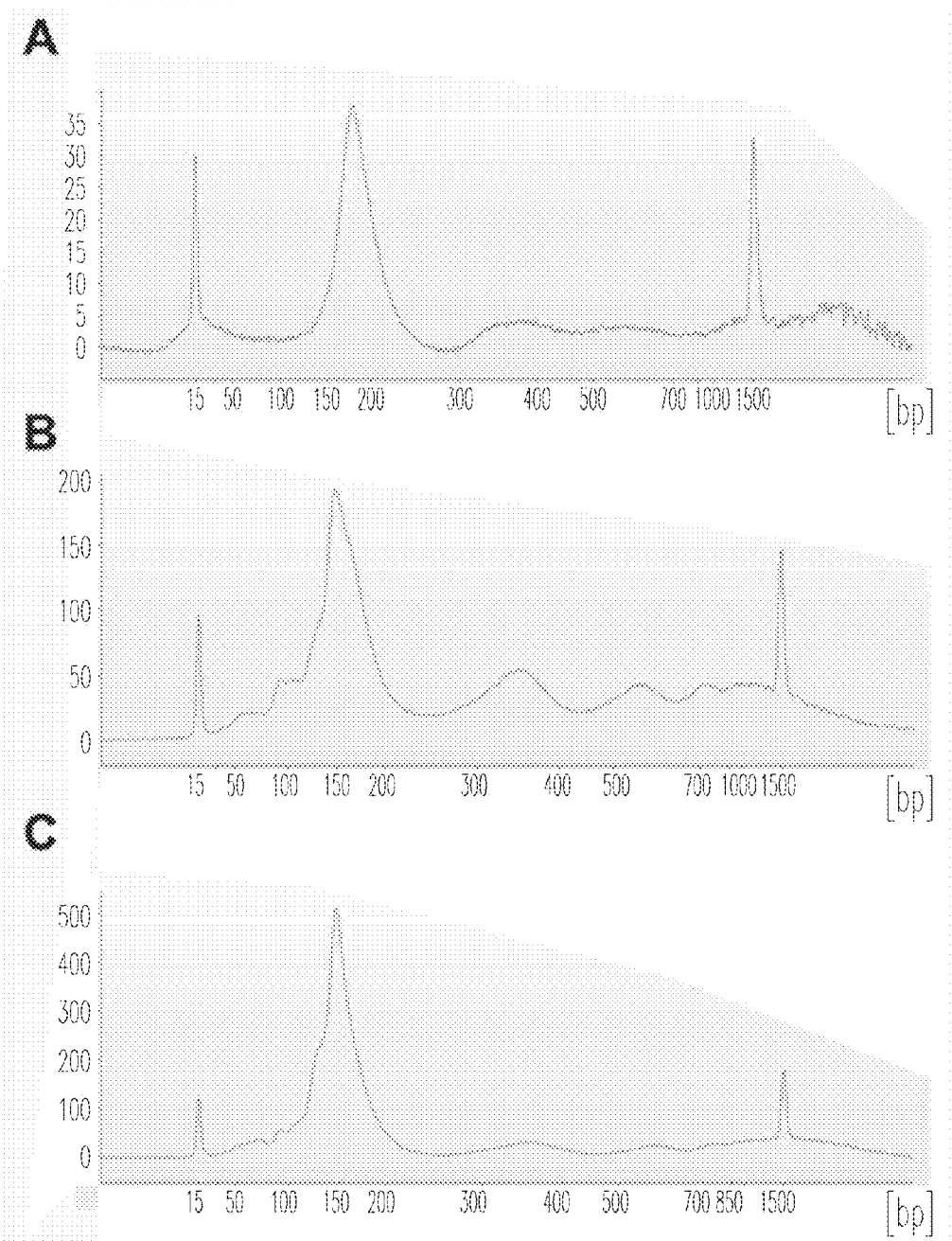
FIG. 1 shows size distributions of natural and artificial cfDNA (cell free). Part A shows mixtures of 96 patient-derived cfDNAs, concentrated 50 fold. Part B shows cell line-derived artificial cfDNA. Part C shows white blood cell-derived artificial cfDNA.

The present invention provides nucleic acid standards that are compositions useful for proficiency testing of laboratories engaging in the analysis of circulating cell-free DNA samples, including cell-free DNA that is used for prenatal genetic analysis or cell-free DNA that is used for the detection or analysis of cancerous cells. These standards are designed to simulate naturally occurring cell free circulating DNA found in the bloodstream of a test subject, e.g., a pregnant woman or suspected cancer patient. It was unexpected that artificially created standards could produce results that were sufficiently close to results obtained from actual patient data so as to provide a useful substitute for a naturally occurring cell-free DNA sample. These artificially created standards can be used to simulate cell-free DNA samples obtained directly from a natural source. Many commercial testing laboratories are regulated, such laboratories have need to develop standardized testing procedures in order to obtain approval or accreditation. The development of such standardized testing procedures can be facilitated by using standards for analysis. A problem with such biological standards is there limited availability. This problem may be addressed using the subject composition and related methods, which can be used to produce large quantities of genetic testing standards, thereby facilitating the commercialization of the tests of interest.

A non-invasive prenatal diagnostic assay can detect and analyze cell-free DNA that is a mixture of maternally derived DNA and DNA derived from the fetus carried by the mother. In some embodiments, the mother may be carrying more than one fetus, e.g. twins, and the subject cell free DNA standard is designed to simulate such cases of multiple births.

Some embodiments of the invention are compositions comprising at least two nucleosomal nucleic acid preparations, wherein each nucleosomal nucleic acid preparation is derived from a different cell source. In some embodiments of the invention, the compositions can comprise more than two nucleosomal nucleic acid preparations derived from different cell sources. In some embodiments of such standards comprise a first nucleosomal nucleic acid preparation derived from a first cell source and a second nucleosomal nucleic acid derived from a second cell source. The different cell sources in a given preparation are different from one another. In various embodiments, different ratios of the nucleosomal nucleic acid preparation components of the subject compositions are provided for, thereby enabling the creation of proficiency testing standards that simulate a given fetal fraction of interest. In some embodiments, different ratios of the nucleosomal nucleic acid preparation components of the subject compositions are provided for, thereby enabling the creation of proficiency testing standards that simulate different stages of cancer.

The subject prenatal nucleic acid proficiency testing standard compositions may be created so as to simulate a wide variety of potential patient samples. The patient samples can vary with respect to the relative amounts of maternally derived cell free nucleic acid to fetal he derived cell free nucleic acid. An additional source of potential variation is chromosomal abnormalities or genetic alleles associated with a genetic disease that are present in the fetus or the mother. Examples of chromosomal abnormalities include various aneuploidies, deletions, copy number variations, translocations, and the like. Examples of aneuploidies include, trisomy 21, trisomy 18, trisomy 13, Turner's syndrome, Klinefelter's syndrome, XYY, XXX, and the like. Additionally, in some embodiments the source of variation may be a genetic allele associated with a genetic disease or carrier state, such as cystic fibrosis, sickle cell anemia, thalassemias, Tay-Sachs disease, Canavan disease, and the like. Similarly, various cancer cells genomes can comprise aneuploidies, deletions, copy number variations, translocations, and the like. The patient samples can vary with respect to the relative amounts cell free nucleic acid derived from the cancer cell of interest and from other non-cancerous cells in the body of the patient.

The ratio of total fetal DNA to total maternal DNA (maternal DNA plus fetal DNA) can, for the sake of convenience, be referred to as the fetal fraction. Embodiments of cell free DNA diagnostic testing standards for prenatal nucleic acid proficiency testing can be produced to mimic a wide variety of potential fetal fractions present in actual maternal cell free circulating DNA samples obtained from pregnant women. Fetal fractions in the range of 1% to 70%, or even higher, as well as all increments within this range can be simulated in various embodiments of the subject compositions. In some embodiments, the subject compositions comprise a first nucleosomal nucleic acid preparation derived from a first cell source and a second nucleosomal nucleic acid preparation derived from a second cell source where in the quantity of the first nucleic acid preparation is greater than the quantity of the second nucleic acid preparation. In some embodiments, the first cell source will be representative of the mother and the second cell source will be representative of the fetus. In some embodiments the second size fractionate nucleic acid preparation will be less than 40% of the total nucleic acid amount in the final preparation. In some embodiments the second size fractionate nucleic acid preparation will be less than 30% of the total nucleic acid amount in the final preparation. In some embodiments the second size fractionate nucleic acid preparation will be less than 20% of the total nucleic acid amount in the final preparation. In some embodiments the second size fractionate nucleic acid preparation will be less than 10% of the total nucleic acid amount in the final preparation.

In embodiments of the invention for use with the analysis of cell-free derived from cancer cells, the ratio of total cell free cancer cell derived DNA to total cell free DNA (cell free cancer cell derived DNA plus other cell free DNA found in the sample) can, for the sake of convenience, be referred to as the cancer cell fraction. Cell-free cancer nucleic acid analysis proficiency testing standards can be produced to mimic a wide variety of cancer cell fractions present in cell free circulating DNA samples obtained from patients or suspected patients. Cancer fractions in the range of 1% to 90%, or even higher, as well as all increments within this range can be simulated in various embodiments of the subject compositions. In some embodiments, the subject compositions comprise a first nucleosomal nucleic acid preparation derived from a first cell source and a second nucleosomal nucleic acid preparation derived from a second cell source where in the quantity of the first nucleic acid preparation is greater than the quantity of the second nucleic acid preparation. In some embodiments, the first cell source will be representative of the mother and the second cell source will be representative of the non-cancerous cells. In some embodiments the second size fractionate nucleic acid preparation will be less than 40% of the total nucleic acid amount in the final preparation. In some embodiments the second nucleosomal nucleic acid preparation will be less than 30% of the total nucleic acid amount in the final preparation. In some embodiments the second size fractionate nucleic acid preparation will be less than 20% of the total nucleic acid amount in the final preparation. In some embodiments the second size fractionate nucleic acid preparation will be less than 10% of the total nucleic acid amount in the final preparation. It will be understood by person skilled in the art that although the previous description refers to a first cell source and a second cell source, embodiments of the invention also provided for that include more than two cell sources, for example the sample may be prepared from one tumor cell line and 3 separate non-tumor cell lines.

The nucleosomal fractions derived from nucleosomal ladders are said to be "fractions" because they do not contain all sizes of the DNA fragments in the nucleosomal preparation derived from the first cell source or the second cell source. By employing nucleosomal nucleic acid preparations, a practical upper size limit is applied, the specific size limit depending on whether mononucleosomal, dinucleosomal, or trinucleosomal fraction containing preparations are used in the particular embodiment.

The compositions include multiple possible combinations of nucleosomal fractions from the first cell source and the second cell source. In some embodiments the nucleosomal nucleic acid preparation prepared from the first cell source comprises (1) the mononucleosomal fraction, the mononucleosomal fraction and the dinucleosomal fraction, or the mononucleosomal fraction and the dinucleosomal fraction and the trinucleosomal fraction. In some embodiments the nucleosomal nucleic acid preparation prepared from the second cell source comprises (1) the mononucleosomal fraction, the mononucleosomal fraction and the dinucleosomal fraction, or the mononucleosomal fraction and the dinucleosomal fraction and the trinucleosomal fraction. The provide embodiments included all possible combinations of the nucleosomal fractions, (1) the mononucleosomal fraction from the first cell source in combination with the mononucleosomal fraction from the second cell source, (2) the mononucleosomal fraction from the first cell source in combination with the mononucleosomal and dinucleosomal fractions from the second cell source, (3) the mononucleosomal fraction from the first cell source in combination with the mononucleosomal, dinucleosomal and trinucleosomal fractions from the second cell source, (4) the mononucleosomal and dinucleosomal fractions from the first cell source in combination with the mononucleosomal fraction from the second cell source, (5) the mononucleosomal and dinucleosomal fractions from the first cell source in combination with the mononucleosomal and dinucleosomal fractions from the second cell source, (6) the mononucleosomal and dinucleosomal fractions from the first cell source in combination with the mononucleosomal, dinucleosomal and trinucleosomal fractions from the second cell source, (7) the mononucleosomal, dinucleosomal, and trinucleosomal fractions from the first cell source in combination with the mononucleosomal fraction from the second cell source, (8) the mononucleosomal, dinucleosomal, and trinucleosomal fractions from the first cell source in combination with the mononucleosomal and dinucleosomal fractions from the second cell source, (9) the mononucleosomal, dinucleosomal, and trinucleosomal fractions from the first cell source in combination with the mononucleosomal, dinucleosomal and trinucleosomal fractions from the second cell source.

Cell Sources

The nucleosomal nucleic acid preparations used to create the subject prenatal nucleic acid proficiency testing standard compositions can be derived from a variety of cell types. Suitable cell types can be primary cells obtained directly from a human subject or can be cell lines that can be propagated in in vitro cell culture. A wide variety of primary cells can be used. Typically primary cells from an easily removable tissue source are used, e.g. blood or a cellular blood fraction such as a buffy coat layer. Similarly, a wide variety of cell lines may be used. Examples of such cell lines include cell lines obtained from the Corriell Institute or the American Type Culture Collection (ATTC).

In some embodiments, the cell sources are from genetically related individuals. Examples of such genetically related individuals are (1) mother and child, (2) mother and multiple children, and (3) mother, father and child. In other embodiments the cell sources are from genetically unrelated individuals. In some embodiments the primary cells are from genetically related individuals. In other embodiments, the cell lines are obtained from genetically related individuals.

In some embodiments, the cell sources are from cells from the same tissue type, wherein one of the cell types is a cancer cell line and the other cell source is a cell line from the same tissue, but not a cancerous cell line.

In some embodiments the first cell source may be from a primary cells and the second cell source may be from a cell line. In some embodiments the first cell source may be from a cell line and the second cell source may be from primary cells.

Nucleic Acid Isolation

The nucleic acids may be isolated from the cell sources by a variety of methods well known to the person of ordinary skill in molecular biology. Typically such methods will involve lysing the cell, thereby liberating nucleic acids so as to leave chromatin structure sufficiently intact to allow the preparation nucleosomal ladders, i.e., nucleosomal preparations. Suitable cell lysis methods include methods in which the nucleus is separately released for subsequent isolation and methods in which the nuclear membrane is dissolved. In some embodiments, the cells may be permeabilized, e.g. using a detergent such as lysolecithin, so as to retain chromatin structure. In some embodiments, the cell membrane may be disrupted by inducing apoptosis in the cells of the cell source.

It is of interest to prepare nucleic acid that are of free of other cellular components so as to enable the biochemical manipulation of the nucleosomal ladders for use in subsequent procedures, e.g. DNA sequencing. In an embodiment of the invention, the commercially available nucleic acid system called AMPURE™ can be used to both purify DNA and isolate nucleosomal fractions of the desired size.

Nucleosomal Ladders

In human cells (as well as other eukaryotic cells) nuclear DNA is organized in the chromatin in nucleosome's in which the chromosomal DNA is organized in approximately 147 base pair units of DNA wrapping around a histone core. The DNA is close proximity to the histone core is relatively resistant to cleavage as compared to the DNA that is present between the nucleosomes. The nucleosomes form a regular pattern in the chromatin, such that exposure of the nucleosomal structures in chromatin to an endonuclease, e.g., micrococcal endonuclease results in a reproducible pattern of a DNA fragments of approximately defined length. This pattern can be visualized by separating the nucleic acid digest fragment based on length, e.g., by electrophoresis.

The histone component of the nucleosome serves to protect the DNA wrapped around the histone core from endonuclease digestion. Fragmenting genomic DNA with a nuclease or fragmenting with a non-enzymatic method (e.g. a chemical digestion with a hydroxyl radical-based reaction, electromagnetic radiation, or sonication) are well known to persons of ordinary skill in the art. Subjecting the chromatin to a digestion reaction results in the formation of a set of nucleic acid fragments approximately 147 base pairs in length and multiples thereof, for the sake of convenience such a set of fragments can be can be referred to as a nucleosomal ladder. A nucleosomal ladder would, for example, appear as a series of bands of different molecular weight when separated by gel electrophoresis. The nucleosomal ladder comprises the approximately 147 base pair fragment and the multiples thereof obtained by digesting the chromatin. The 147 base pair fragment is referred to as the mononucleosomal fraction of the nuclear ladder. The two-fold multiple of the mononucleosomal fraction is referred to as the dinucleosomal fraction and is formed by nucleases (or other DNA cleavage agents) cleaving DNA adjacent to two nucleosomes (but leaving the internucleosomal region intact). The three-fold multiple of the mononucleosomal fraction is referred to as the trinucleosomal fraction and is formed by nucleases (or other DNA cleavage agents) cleaving DNA adjacent to three nucleosomes (but leaving the internucleosomal region intact) It will be understood by person skilled in the art of molecular biology that nuclease cleavage (or other DNA cleavage agents) is imprecise and can give rise a set of nucleic acid fragments of similar, but not identical size.

In some embodiments of the invention the nucleosomal ladders may be produced by inducing apoptosis in cells. As a part of apoptosis process, endogenous endonucleases cleave the DNA component of the chromatin so as to form nucleosomal ladders. In some embodiments of the invention the nucleosomal ladders may be produced by digesting the chromatin with an endonuclease, e.g., micrococcal endonuclease. In other embodiments of the invention the nucleosomal ladder may be produced by exposing the chromatin to digestion with non-enzymatic agents.

AMPURE™ can be used to both purify DNA and isolate nucleosomal fractions of the desired size. In other embodiments, nucleosomal fractions of the desired size can be obtained by gel electrophoresis separated fragment purification, purification from HPLC, or purification through ultracentrifugation.

Manipulation of Nucleosomal Fractions

In some embodiments, the nucleosomal fractions, mononucleosomal, dinucleosomal, trinucleosomal, and various combinations thereof may be manipulated so as simulate one or more genetic abnormalities, such as a duplication, deletion, or point mutation. For example, a deletion may be simulated by exposing nucleosomal preparations to a solid support comprising nucleic acids (or analogs thereof) to selectively bind to the region to be deleted, thereby producing a preparation containing a greatly reduced amount of the region to be deleted. Similarly, point mutations may be introduced by techniques such as PCR performed on the nucleosomal fractions.

Analysis of Cell Free Fetal DNA in the Maternal Blood Stream

The subject compositions for prenatal nucleic acid proficiency testing can be used in a wide variety of prenatal genetic testing methods. The proficiency testing standards are used essentially the same as a sample obtained from a test subject, thereby providing a meaningful standard from the specific test being evaluated. Such methods of noninvasive prenatal genetic testing typically involve the analysis of cell free nucleic acids found in the bloodstream of a pregnant woman. In some embodiments, the prenatal genetic testing method involves non-directed sequencing of the cell free nucleic acids such as in U.S. Pat. No. 8,296,076 B2, U.S. Pat. No. 8,008,018 B2, U.S. Pat. No. 7,888,017 B2, U.S. Pat. No. 8,467,976 B2. In other embodiments, the directed analysis of specific polymorphic regions or specific non-polymorphic regions, such as in patent applications US 2013/0143213 A1, US 2013/0172211 A1, US 2012/0270212 A1, US 2012/0122701 A1, US 2013/0123120 A1, US 2011/0178719 A1, can be employed.

Analysis of Cell Free DNA for Cancer Cell Derived DNA

Various protocols are known to the person or ordinary skill in the art for analyzing cell free DNA circulating in the blood stream or other tissue, but ultimately derived from cancerous cells, for example, see publications such as: Circulating Cell-Free DNA in Plasma/Serum of Lung Cancer Patients as a Potential Screening and Prognostic Tool, Pathak et al, Clinical Chemistry October 2006 vol. 52 no. 10 1833-1842; Cell-free Tumor DNA in Blood Plasma As a Marker for Circulating Tumor Cells in Prostate Cancer, Schwarzenbach et al, Clin Cancer Res Feb. 1, 2009 15; 1032; Cell-free DNA: measurement in various carcinomas and establishment of normal reference range, Wua et al, Clinica Chimica Acta, Volume 321, Issues 1-2, July 2002, Pages 77-87; Detection of Circulating Tumour DNA in the Blood (Plasma/Serum) of Cancer Patients, Anker et al, Cancer and Metastasis Reviews 1999, Volume 18, Issue 1, pp 65-73; Cell-free nucleic acids as biomarkers in cancer patients, Schwarzenbach et al, Nature Reviews Cancer 11, 426-437 (June 2011); Circulating Tumor-Specific DNA: A Marker for Monitoring Efficacy of Adjuvant Therapy in Cancer Patients, Fiegl et al, Cancer Res Feb. 15, 2005 65; 1141.

The following examples are offered for purposes of illustration only and should not be construed as limiting the claimed inventions.

EXAMPLES

Example 1

Developing Synthetic Pregnancy Plasma Samples for Use in Non-Invasive Prenatal Testing Introduction:

Cell-free DNA (cfDNA)-based non-invasive prenatal testing (NIPT) allows for the identification of fetal aneuploidies from the mixture of maternal and fetal cfDNA (cell free DNA) in maternal circulation using next-generation sequencing-based approaches. Such tests are revolutionizing prenatal screening and fetal aneuploidy detection. However, cfDNA is a mixture of maternal and fetal cfDNA, and both the overall amount of cfDNA as well as the fraction of cfDNA from the fetus can be limiting. This limits the number of analyses that can be performed on a single sample (e.g. for development and proficiency testing). Additionally, validating NIPT performance on rare disorders is challenging as patient recruitment is limiting. To overcome these challenges, a novel method for creating an artificial pregnancy plasma DNA (plasmART) was invented.

Methods:

DNA was isolated from primary cells or cultured immortalized cells and treated to generate nucleosomal-size ladders (mono-, di-, and tri-nucleosome-size fragments). These ladders mimicked observed cfDNA fragment lengths, which are derived from genomic DNA digested by apoptotically-activated nucleases. This includes shorter "fetal" fragments and a combination of shorter and longer "maternal" fragments. To simulate pregnancy plasma, the maternal and child "cfDNAs" were mixed at various ratios to mimic a range of fetal fractions. These mixtures were then examined using the Natera Panorama NIPT, which employs the advanced Next-generation Aneuploidy Test Using SNPs (NATUS) algorithm. The NATUS algorithm reports copy number for each chromosome with an associated confidence.

Results:

This approach allowed for the identification of the fetal fraction influence on test accuracy on the same mother-child pair, rather than comparing accuracy over fetal fractions encountered from distinct pregnancies in the population. The performance of the Natera Panorama NIPT was examined on mixtures of maternal and child samples. NIPT correctly distinguished affected and unaffected "pregnancy" plasmARTs, suggesting that these mixtures behave similarly to cfDNA isolated from maternal plasma. The ability to call chromosome copy number with high confidence at fetal fractions of below 5% correlated well with true pregnancy plasma samples Example 2

Cell Free DNA Testing Standards for Genetic Disorders

Non-invasive Prenatal Screening (NIPS) to conditions that are rare and not routinely screened for in pregnancy is challenging. The collection of sufficient samples to confidently validate test performance is essentially impossible. Further, the samples that are collected are almost always identified after an invasive procedure and therefore of later gestational age and higher fetal fraction. As fetal fraction is a crucial parameter affecting performance of all NIPS, using exclusively higher fetal fraction samples may result in inflated claims of test sensitivity. Therefore, an alternative approach to validating NIPS for rare disorders is needed to adequately estimate test performance. A method to generate artificial cfDNA samples (plasmArt), i.e., cell-free DNA DNA diagnostic testing standards, for use in testing and validation that mimic the size distribution of natural cfDNA. PlasmArt can be generated from lymphoblastoid cell lines or white blood cells (i.e. buffy coat) of normal or affected individuals. Once prepared, plasmArt from two individuals, such as a mother and her child, can be combined to simulate pregnancy cfDNA at any desired ratio, enabling simulation of the fetal fractions observed in real populations. To generate artificial samples that mimic natural cfDNA, we sought to replicate the mechanism of cfDNA fragmentation in vitro. An individual's cfDNA predominately arises from apoptosis of cells in the hematopoietic system (Lui Y Y, Chik K W, Chiu R W, Ho C Y, Lam C W, Lo Y M. Clin Chem. 2002; 48:421-7). During apoptosis, the Caspase-Activated DNase (CAD) is activated by Caspase-3 cleavage of the CAD inhibitor. The activated nuclease preferentially cleaves DNA between nucleosomes (Widlak P. Acta Biochim Pol. 2000; 47:1037-44), resulting in the characteristic mono-, di-, and tri-nucleosomal-sized DNA fragments observed in cfDNA (Li Y, Zimmermann B, Rusterholz C, Kang A, Holzgreve W, Hahn S. Clin Chem. 2004; 50:1002-11; Fan H C, Blumenfeld Y J, Chitkara U, Hudgins L, Quake S R. Clin Chem. 2010; 56:1279-86.). Each nucleosome coordinates approximately 146 nucleotides of DNA (Luger K, Mader A W, Richmond R K, Sargent D F, Richmond T J. Nature. 1997; 389:251-60.). Based on the intranucleosomal nuclease activity that generates cfDNA, we used micrococcal nuclease (MNase), which has a similar biochemical activity of cleaving preferentially between nucleosomes (Widlak P, Li P, Wang X, Garrard W T, J Biol Chem. 2000; 275:8226-32; Allan J, Fraser R M, Owen-Hughes T, Keszenman-Pereyra D. J Mol Biol. 2012; 417:152-64.). Previous methods to generate artificial cfDNA from pregnancy samples have relied on sonicated DNA (Srinivasan A, Bianchi D W, Huang H, Sehnert A J, Rava R P. Am J Hum Genet. 2013; 92:167-76). However sonication results in broad fragment size distributions (peak size 200 nucleotides+/−100) (See http://www.diagenode.com/en/applications/dna-Shearing-.php for a description of sonication sizes and distributions), and start sites are not constrained by nucleosome position. By employing an enzyme with a similar biochemical activity to the in vivo nuclease involved in fragmentation, the cell-free DNA DNA diagnostic testing standards, e.g., plasmArt, preparation method described herein approximates the size and cleavage biases observed in natural cfDNA.

Results

In Vitro Recapitulation of the Fragmentation Profile Observed in Cell Free DNA

Artificial samples should approximate the size distribution of cfDNA observed in vivo to capture potential biases introduced during library construction. Library preparation PCR typically favors short fragments over long, thus post amplification only short fragments will be represented. We first confirmed the nucleosomal ladder pattern observed in natural cfDNA from samples purified in the Natera clinical laboratory. To overcome the low concentration of natural cfDNA, the cfDNA from 96 pregnant individuals was mixed in equal volumes, concentrated approximately 50 fold, and examined on a Bioanalyzer (FIG. 1A). The mononucleosomal peak is present at 180 nucleotides. A dinucleosomal peak is present at 382 nucleotides. PlasmArt was prepared from cell lines (FIG. 1B) and white blood cells (FIG. 1C). PlasmArt from cell lines displays a mononucleosomal peak at 148 nucleotides and the dinucleosomal peak at 349 nucleotides. For white blood cells, the mononucleosomal peak is at 146 nucleotides and the dinucleosomal peak is at 359 nucleotides. Thus the method for creating plasmArt results in a DNA fragment profile similar to natural cfDNA. The location of the peaks suggests that natural cfDNA are larger than artificial cfDNA fragments, but this is consistent with the observation that CAD releases larger fragments than MNase, likely due to a higher activity of MNase in vitro. Overall plasmArt is more similar than other methods used to create artificial cfDNA, and we expect that size difference has a minimal effect. In fact, the small fragments produce a more challenging sample type for PCR assay methods that require that target SNPs be flanked by two intact primer binding sites, a less likely occurrence as DNA fragments become smaller.

FIG. 1 shows size distributions of natural and artificial cfDNA (cell free). Part A shows mixtures of 96 patient-derived cfDNAs, concentrated 50 fold. Part B shows cell line-derived artificial cfDNA. Part C shows white blood cell-derived artificial cfDNA.

Mixtures of Mononucleosomal Mother and Child Simulate Real Samples

In addition to mimicking the size distribution of natural cfDNA, mixtures of mother and child plasmArt samples must have similar NIPS performance to pregnancy cfDNA samples. PlasmArt was generated from cell lines purchased from the Coriell Cell Repository: GM11388 (child) and GM11389 (mother). Four independent mixtures of mother and child were made such that the molar ratios were 3%, 6%, 9%, and 12% child. These samples were used as input into Panorama™ NIPS. The fetal fraction calculated by the algorithm for these samples were 3.5%, 6.3%, 9.1%, and 12.0%, respectively (FIG. 2, $R2=0.99$, slope=0.94), indicating a near perfect correlation between input child amount and measured fetal fraction in Panorama™.

Figure 2:
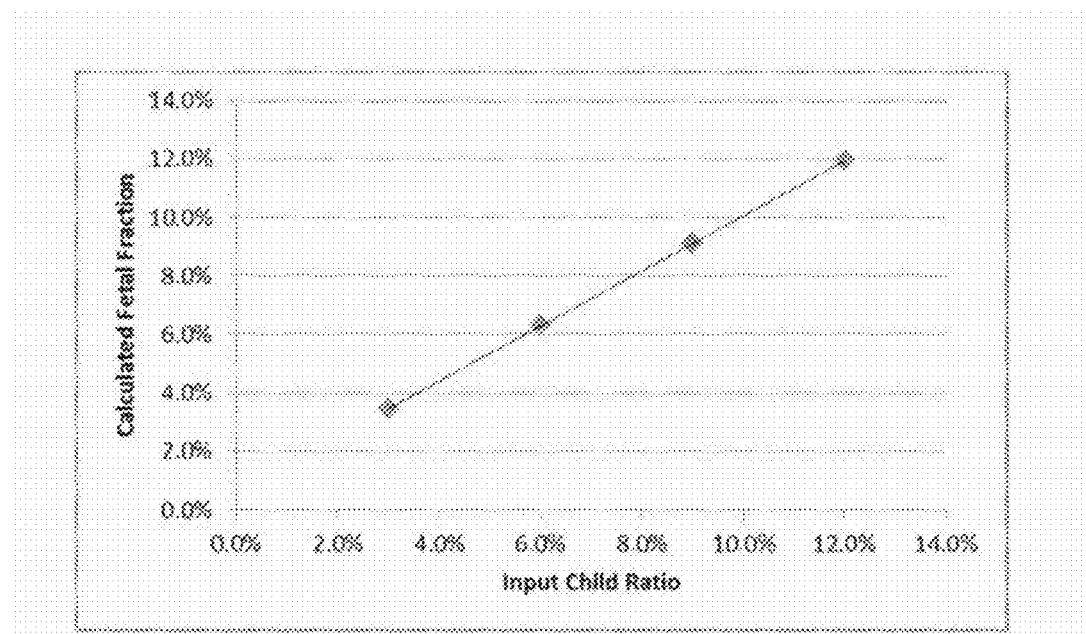
FIG. 2 shows calculated fetal fractions as a function of input child amount.

FIG. 2. Calculated Fetal Fractions as a function of input child amount. 4 independent mixtures were generated from one mother/child pair, tested in the Panorama™ workflow, and examined for the calculated fetal fraction. The $R2=0.99$ and the slope=0.94.

Figure 3:
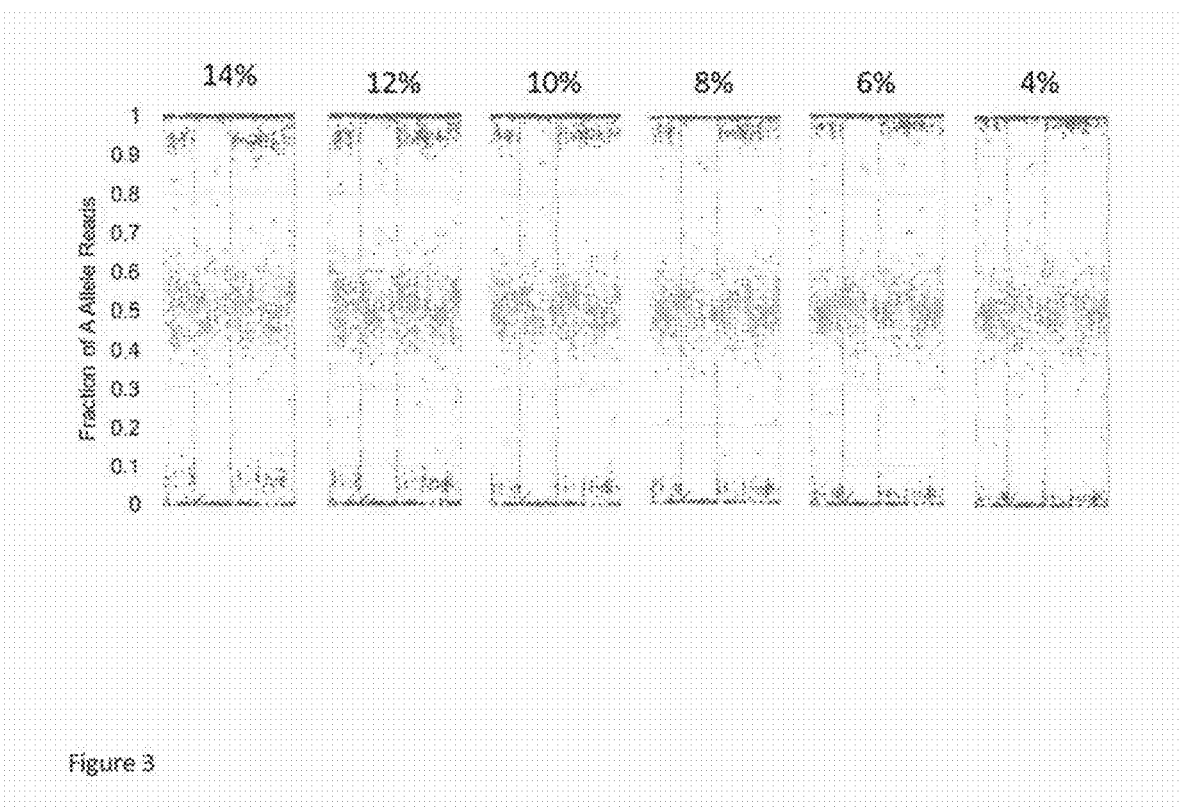
FIG. 3 shows a plot of the allele ratios of the SNPS analyzed at different fetal fraction concentrations.

Having demonstrated the ability to make predictable mixtures of mother and child, we examined the ability to detect a paternally contributed 22q11.2 microdeletion. If a microdeletion originates in the father, the lack of paternally contributed SNPs can be visualized on allele frequency plots (FIG. 3). In this case, there are no paternally contributed SNPs in the 22q11.2 region, while there are paternally contributed SNPs in other genomic regions. This 22q11.2 deletion can be observed from low fetal fraction (4%) to a relatively high fetal fraction (14%), and all intermediate fetal fractions. Taken together, these data show that child DNA can be mixed into mother DNA in predictable amounts, and mixtures can be analyzed to identify known microdeletion syndromes.

FIG. 3. Paternal 22q11.2 deletions can be detected over a range of fetal fractions. At each fetal fraction, 3 different genomic regions are shown adjacent to one another— 17p11.2, 22q11.2, and 22q13.

"A" allele ratios from individual binary SNPs ["A" allele reads/("A"+"B" reads)] are shown in ascending order on the X axis by genomic region, then by SNP chromosome location. Data points are colored according to maternal genotype (AA, red; BB, blue; AB, green). In pregnancy cfDNA and plasmArt, the father's contribution to the mixture can be most readily observed as blue or red points offset from the 0% or 100% A allele fractions (maternal BB and AA points, respectively). These are SNPs for which the mother is homozygous AA or BB, but has the fetus or mixed in child sample contributes a B or A allele respectively. For instance, at 10% fetal fraction, the mixed in child sample's contribution can be visualized as points centered at 5% and 95%, since one half of the sample mixed in at 10% corresponds to the A or B allele respectively. The absence of any contribution from the paternal SNPs observed at all fetal fractions for the 22q11.2 region is consistent with a paternally contributed microdeletion of this region. This titration demonstrates the ability to detect a paternally contributed microdeletion over a wide range of fetal fractions, down to 4%.

We next examined the ability to detect maternally contributed microdeletions. Fifteen plasmArt samples were made over a broad range of fetal fractions from a Coriell Cell Repository Angelman Syndrome family: GM11517 (mother) and GM11516 (child). Angelman Syndrome is caused by a maternally contributed deletion of 15q11.2-q13. The calculated fetal fractions were 6.8%, 7.8%, 8.4%, 10.0%, 10.8%, 11.8%, 13.0%, 14.4%, 14.6%, 15.2%, 16.7%, 18.6%, 20.4%, 21.3%, and 24.6%. Unlike paternal deletions, maternally inherited deletions result in subtler changes to the allele ratios and are difficult to detect visually on Allele Ratio Plots. Thus, the Panorama™ NATUS algorithm, modified to detection segmental deletions was employed to examine maternal deletions. The algorithm correctly identified the deletion in all 15 of the plasmArt samples. Importantly, in these samples the algorithm also evaluated copy number of the 22q11.2, Cri-du-chat, and 1p36 regions. The algorithm correctly identified 44 of 45 regions (3 regions by 15 samples) as normal, no deletion detected. The algorithm did not return a high confidence result for the 22q11.2 region of the 6.8% sample. The observed sensitivity and specificity of these initial tests indicate that plasmArt can be used for developing and validating NIPS for rare syndromes.

Conclusion

It was demonstrated that the cell-free DNA standard prepared using MNase in vitro more faithfully recapitulates the size distribution of natural cfDNA than sonication. MNase treatment of either cell lines or white blood cells gave similar results that were comparable to natural cfDNA size distributions. Next, we showed that mixtures of various amounts of mother and child plasmArt samples correlated very well with the fetal fractions measured by the NATUS algorithm. Finally, we demonstrated that plasmArt mixtures could be used to simulate pregnancy cfDNA samples at various fetal fractions having a paternally-inherited 22q11.2 deletion and a maternally-inherited Angelman deletion. For each of these simulated groups, the NATUS algorithm correctly identified the deletions and the unaffected regions.

These results suggest that plasmArt can be used as a tool for validating rare disorders in the context of NIPS.

Example 3

Tumor Standards for Copy Number Variants (CNV)

Materials and Methods
Samples

Assay validation was performed using five human breast cancer cell lines (HCC38, HCC1143, HCC1395, HCC1954, and HCC2218) along with matched normal cell lines; these cell lines and matched genomic DNA (gDNA) samples were obtained from American Type Culture Collection (ATCC). Paired father and child cell lines (GM10383 and GM10382 respectively) for producing cell-free nucleic acid standards (details below) were obtained from the Coriell Cell Repository (Camden, N.J.). The child of this cell line is a DiGeorge Syndrome (DGS) proband with a maternal deletion and thus the child cell line has only the paternal DGS 22q11 region; the parental origin of the deletion was determined by our SNP-based mmPCR assay (data not shown).

Tumor tissues from 14 breast cancer patients were obtained from Geneticist (Glendale, Calif.) and North Shore-LIJ (Manhasset, N.Y. In addition, matched buffy coat (4 patients) and matched plasma samples (9 patients) were obtained. Blood from each subject was collected into EDTA tubes, and cfDNA was isolated from 1 ml plasma using the QIAamp Circulating Nucleic Acid Kit (catalog no. 55114, Qiagen, Valencia, Calif.) according to the manufacturer's instructions.

Cell Culture

All cell culture reagents (culture media and fetal bovine serum [FBS]) were obtained from Life Technologies (Foster City, Calif.). ATCC cell lines were cultured according to the ATCC cell culturing, passaging, and cryogenic storage guidelines. Cells were cultured in 10% FBS RPMI 1640 (high glucose with pyruvate) with 2 mM L-Glutamine at 37° C. with 5% CO2. Seed stocks were made of each cell line after one passage, and a cut off of five passages was chosen in order to preserve the genetic stability of each cell line. Cells from the Coriell Cell Repository were grown according to manufacturer's instructions: GM10382 in 15% FBS DMEM and GM10383 in 15% FBS RPMI 1640. Cells were washed twice in DPBS to remove FBS and culture media before DNA isolation.

Single cells were isolated from cultures manually using an inverted phase-contrast microscope. A serial-dilution method was implemented involving pipet transfers of single media droplets containing cells in suspension onto the surface of a petri dish. Subsequently, small volumes of the original cell suspension droplet were mixed into droplets of phosphate buffered saline in a serial dilution until visualization of a single intact cell was achieved. Single cells were transferred to a PCR plate (1 cell per well) and lysed using a lysis buffer consisting of Salt Mix (1M KCl, 25 mM MgCl2, 0.1M Tris-HCl), 0.1M DTT, and the Arcturus PicoPure DNA Extraction Kit from Applied BioSystems. After the lysis buffer is added to each well, the plate is run on the following thermal cycler protocol: 56° C. for 1 hr, 95° C. for 10 min, 25° C. for 15 min, 4° C. hold. The single genomic copies were then used as templates for a PCR reaction.

Genomic DNA Isolation

Genomic DNA from fresh frozen (FF) tissue was extracted using the DNeasy Blood and Tissue Kit (catalog no. 69506, Qiagen), according to the manufacturer's spin-column protocol for purification of total DNA from animal tissues. DNA was extracted from FFPE samples with the QIAamp DNA FFPE Tissue Kit (catalog no. 56404, Qiagen) according to the manufacturer's instructions.

Cell-Free Nucleic Acid Standard Generation

A proof-of-concept plasma model system was established by generating fragmented DNA mixtures for use as cell-free nucleic acid size standards that resemble the size profiles of the cell-free DNA (cfDNA) naturally found in plasma. To start, 9×106 cells were lysed in hypotonic lysis buffer (20 mM Tris-Cl pH 7.5, 10 mM NaCl, 3 mM MgCl2) for 15 minutes on ice before 10% Igepal CA-630 (Sigma, St. Louis, Mo.) was added to a final concentration of 0.5%. Nuclei were pelleted by centrifugation at 3,000×g for 10 minutes at 4° C., and then resuspended in 1× MNase Buffer (New England BioLabs, Ipswich, Mass.) before 1000 U of MNase (New England BioLabs) was added. Resuspended nuclei were incubated for 5 minutes at 37° C. to facilitate MNase digestion. Reactions were stopped by the addition of EDTA to a final concentration of 15 mM. Undigested chromatin was removed by centrifugation at 2,000×g for 1 minute. Fragmented DNA was purified using the DNA Clean & Concentrator™-500 kit (catalog no. D4032, Zymo Research, Irvine, Calif.) according to manufacturer's instructions. Fragmentation was confirmed by running the purified samples on a Bioanalyzer DNA 1000 chip (Agilent, Santa Clara, Calif.). Mononucleosomes were purified by a 2-step purification strategy using AMPure XP (Beckman Coulter, Brea, Calif.). First, to remove large fragments, 0.9× AMPure XP beads were added and allowed to bind before magnetic removal. Next, the supernatant was transferred to a fresh tube, additional AMPure XP beads were added to 2×, and DNA was purified according to manufacturer's instructions. Mononucleosomal DNA fragment size (approximately 150 nt) was confirmed by running the samples on a Bioanalyzer DNA 1000 chip (Agilent).

Child DNA was titrated into the corresponding father DNA to achieve artificial mixtures with different child DNA fractions. This method generates cell-free size standards with 22q11 region CNVs which mimic cancer plasma samples with variable imbalance between copies of the two 22q11 homologs. Pure father samples were run as controls. Cell-free size standards from cancer cell lines (HCC1954 and HCC2218) were also generated by titrating with the corresponding matched normal cell line (HCC1954BL and HCC2218BL, respectively).

Validation of Tissue Samples

Chromosomal microarray analysis on fresh frozen tissue samples was performed using the Illumina CytoSNP-12 97 genotyping microarray platform as previously described [1]. Analysis of FFPE tissue samples using the Affymetrix OncoScan microarray platform was carried out according to the manufacturer's protocol.

Massively Multiplex PCR and Sequencing

For the 27,744-plex protocol, samples were pre-amplified for 15 cycles using PCR and 27,744 target-specific assays, an aliquot was then transferred to a second nested 15-cycle PCR reaction. Amplified samples were prepared for sequencing by adding barcoded tags in a 12-cycle PCR reaction. Thus, for the 28,000-plex protocol, 27,744 targets were amplified in a single reaction; targets included SNPs from chromosomes 1, 2, 13, 18, 21 and X, and regions 1p36, 4p16, 5p15, 7q11, 15q11, 17p13, 17p11, 22q11, and 22q13. A modified version of this protocol was used for the 3,000-plex approach where 3,168 target-specific assays were amplified using a 25 cycle PCR reaction allowing a focused analysis of SNPs from chromosomes 1 and 2 and the 22q11 focal region. Sequencing of amplicons was carried out using an Illumina HiSeq 2500 sequencer; x tissue samples or 8-12 plasma samples were sequenced per run.

Data was plotted with the relative fraction of one allele (arbitrarily chosen) on the y-axis, and the SNP location along the chromosomal region on the x-axis such that the observed allele fractions at each of the chromosomal regions indicate the overall proportion of the two haplotypes present in the sample; note that sample heterogeneity may confound precise determination of the relative copy number of the two haplotypes in any given cell from measurements made on bulk sample.

Data Analysis

Allelic data distributions were modeled for the following hypotheses: (i) all cells are normal, (ii) presence of cells with a homolog 1 deletion and (iii) presence of cells with a homolog 2 deletion. The likelihood of each of the hypotheses was calculated based on observed Next Generation Sequencing (NGS) data at multiple heterozygous SNPs; sequencing and PCR related errors were taken into account. The algorithm compares predicted distributions with actual allelic distributions as measured from the sample in question, employing a Bayesian-based maximum likelihood approach to determine the relative likelihood of each hypothesis given the observed data across multiple tumor fractions and using the haplotype information deduced from the tumor sample corresponding to the same individual. For example, consider a heterozygous SNP with genotype AB (with dimorphic alleles arbitrarily labeled as A and B). If the homolog with allele A is deleted in some cells, then we expect the ratio of A reads to total reads to go down. Similarly, if the homolog with allele B is deleted, then we expect the ratio of B reads to total reads to go down. The change in this ratio is proportional the fraction of tumor DNA present in the plasma. For cases where one of the deletion hypotheses is more likely than the normal hypothesis across a sufficiently large range of tumor fractions, tumor DNA quantity is determined using a maximum likelihood estimation method across those tumor fractions, otherwise tumor DNA fraction is estimated to be equal to zero.

Validation of CNV Approach

The capacity of this SNP-based massively multiplex PCR (mmPCR) approach to accurately detect CNVs (copy number variants) was established using four separate methods, described below. The performance of the assay was demonstrated using, as input, gDNA, both from large numbers of cells and from single cells, DNA from FFPE tissue, and artificial cell free DNA testing standards that simulate cell free circulating tumor DNA (ctDNA) made by mixing appropriately sized DNA from the tumor and germ line samples.

First, an assay targeting 27,744 SNPs dispersed across 6 whole chromosomes and 9 additional focal regions that cover common deletion syndromes were used to analyze gDNA from 71 characterized cell-line samples having a single deletion in one of the eight deletion syndrome regions; p- and q-arms were analyzed separately. Sensitivity was 100% (71/71) and specificity, including all normal regions among affected samples and an additional 25 unaffected samples, was also 100% (1,849/1,849).

Second, six characterized cancer cell lines and XX normal cell lines were analyzed using a 3,168-plex, a 27,744-plex PCR and a SNP microarray. Visual inspection of the plotted allele fractions showed similar fractions over all regions with apparent copy number variations (representative plots shown). Data was plotted with the relative fraction of one allele (arbitrarily chosen) on the y-axis, and the SNP location along the chromosomal region on the x-axis such that the observed allele fractions at each of the chromosomal regions indicate the overall proportion of the two haplotypes present in the sample; note that sample heterogeneity may confound precise determination of the relative copy number of the two haplotypes in any given cell from measurements made on bulk sample. To show that the assay has single molecule sensitivity, individual cells were isolated from the aforementioned cancer cell lines, and were analyzed as described above Plotted allele fractions from single cells were similar to both those observed from large quantities, and also SNP arrays, with minor allowances made for expected heterogeneity. To mimic a heterogeneous tumor profile, and determine the capacity for this method to detect CNVs present in a subpopulation of cells, cancer cells were mixed with normal cells at different ratios. Using a linear titration of the cancer cell line HCC2218 into the matched normal control cell line, a corresponding linear change in the allele ratio was determined.

Third, the ability of this methodology to accurately detect CNVs in tumor tissue was validated by visual comparison of three FF tissue samples using the 3,000-plex PCR and SNP microarray; similar allele fractions were observed. Buffy coat samples from each of the samples were included as germline controls; no CNVs were detected in these samples by either method. The same mmPCR methodology was successfully applied to detect CNVs from formalin fixed paraffin embedded (FFPE) tissue samples, which typically pose a challenge to SNP microarrays. Similar allele fraction patterns were observed among three tumor samples using the 3,000-plex PCR approach and Affymetrix Oncoscan, a commercially available assay that is capable of evaluating CNVs from FFPE samples (two examples are shown in. Importantly, no modifications of the multiplex PCR method were required to characterize the FFPE samples.

To determine whether the CNVs detected in the tumor tissue samples were somatic CNVs a subset of 13 breast cancer samples which had buffy coat, adjacent non-tumor tissue and tumor tissue samples available were analyzed. No CNVs were observed in any of the buffy coat samples, while CNVs were detected in 84.6% (11/13) of the tumor tissue samples. In xx % (x/13) of non-adjacent tumor tissue samples, CNVs were observed (give details, were they the same CNVs as in tumor tissue etc.).

Fourth, validation of ctDNA quantification in plasma samples was carried out using artificial cell-free DNA standards (Plasmart) mimicking plasma ctDNA. Cell-free nucleic acid standards corresponding to ctDNA were created in one of two ways: Cell-free nucleic acid standards corresponding to ctDNA with well characterized CNVs were created by titrating DNA from a child a known CNV in the 22q11.2 region resulting from deletion of the maternal haplotype, into the corresponding father's DNA, which had a normal copy number at the 22q region. Alternately, cell-free nucleic acid standards for tumors were created by titrating tumor cell lines with the corresponding matched normal cell lines (see Materials and Methods). Prior to mixing, the DNA of the samples was processed enzymatically to recreate the DNA fragment size distribution observed in natural cell-free DNA which is derived from an apoptotic process. The limit of quantitation (LOQ) is defined as the lowest concentration at which a mutation could be reliably detected with a given level of accuracy and precision. To determine the LOQ, cell-free nucleic acid standards containing various child: father DNA ratios corresponding to ctDNA levels of 0-10% and cell-free nucleic acid standards containing various tumor: matched normal DNA ratios corresponding to ctDNA levels of 0-50% were run. Copy number variations were detected in samples above 0.2% "ctDNA" or above 0.45% "ctDNA" shown in FIG. 4. There were 12 samples per run, and the DOR per SNP.

Application of mmPCR Approach

Following validation of the mmPCR (massively multiplexed PCR) method, the technique was applied to the detection of CNVs in tumor tissue and plasma samples from 97 cancer patients. The 3,000-plex mmPCR method focusing on five chromosomal regions was applied for analyses of CNVs in these samples as this focused approach allows a greater depth of read. Overall, somatic copy number variations were detected in at least one of the five regions assayed in 88.9% (40/45) of breast tumor tissue samples, 66.7% (16/24) of lung tumor tissue samples and 46.4% (13/28) of colon tumor tissue samples and were detected across all five regions-of-interest evaluated. The regions-of-interest included in this panel were not focused on cancer related CNVs; use of a targeted panel of CNVs commonly associated with cancer would be expected to provide significantly greater coverage.

The ability of the mmPCR method to detect the somatic CNVs observed in the tumor tissue in the matched patient plasma samples was then investigated. Overall, copy number variations were detected in x/40 of breast plasma samples, y/16 of lung plasma samples and z/13 of colon plasma samples), and were detected across all five regions-of-interest evaluated.

Tumor Heterogeneity

One of the potential advantages of liquid biopsies is that ctDNA may reveal the spectrum of tumor-associated mutations that exist in the tumor, unlike a focal tumor biopsy that could miss some or all tumor-associated CNVs because of tissue heterogeneity. To determine the effects of tumor heterogeneity on the detection of CNVs in plasma versus focal biopsies, a number of subsections from eight breast cancer samples were analyzed, and compared to the matching plasma sample. XX/40 regions assayed in the 8 samples showed significant heterogeneity between biopsies. Of the 40-XX regions that were mostly homogenous, Q involved a CNV, and W/Q of those CNVs were observed in the plasma. In the Y/XX of the regions where there was a CNV in at least one of the biopsies, the CNV was observed in B/Y of the plasma. Interestingly, one of these samples had a CNV on 22q11 detected in the plasma that was not visible in some of the tumor tissue sections, while a second sample had a CNV on 1q detected in the plasma that was not visible in some of the tumor sections It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, many of the methods, compositions described above can be used in various combinations.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

Outline of Some Embodiments of Invention

An outline of various embodiments of the invention is provided below in claim format.

1. A cell-free nucleic acid diagnostic proficiency testing standard composition, comprising,
   a first nucleosomal nucleic acid preparation derived from a first cell source, and
   a second nucleosomal nucleic acid preparation from a second cell source,
   wherein the quantity of the first nucleic acid preparation is greater than the quantity of the second nucleic acid preparation.

2. The prenatal nucleic acid proficiency testing standard composition according to claim 1, wherein the first nucleosomal nucleic acid preparation is derived from a primary cell source.

3. The prenatal nucleic acid proficiency testing standard composition according to claim 1, wherein the first nucleosomal nucleic acid preparation is derived from a cell line.

4 A composition according to claim 1, wherein the first cell source and the second cell source are cell lines.

5 A composition according to claim 1, wherein the first cell source and the second cell source are primary cell sources.

6 The method of claim 1, wherein the first cell source is a primary cell source and the second cell source is a cell line.

7 The composition of claim 1, wherein the second cell source is a primary cell source and the first cell source is a cell line.

8 The composition according to claims 1-7, wherein the first cell source is genetically related to the second cell source.

9 The composition according to claims 1-7, wherein the first nucleosomal nucleic acid preparation has been prepared with an endonuclease.

10 The composition according to claims 1-7, wherein the first nucleosomal nucleic acid preparation has been prepared with a micrococcal endonuclease.

11 The composition according to claims 1-7, wherein the first nucleosomal nucleic acid preparation has been prepared with an endonuclease.

12 The composition according to claims 1-7 wherein the first nucleosomal nucleic acid preparation and the second nucleosomal nucleic acid are nucleosomal ladder fractions.

13 The composition according to claim 12, wherein the first nucleosomal nucleic acid preparation and the second nucleosomal nucleic acid comprise mononucleosomal ladder fractions.

14 The composition according to claim 13, wherein the first nucleosomal nucleic acid preparation comprises dinucleosomal ladder fractions.

15 The composition according to claim 14, wherein the first nucleosomal nucleic acid preparation comprises trinucleosomal ladder fractions.

16 The composition according to claim 13, wherein the second nucleosomal nucleic acid preparation comprises dinucleosomal ladder fractions.

17 The composition according to claim 16, wherein the second nucleosomal nucleic acid preparation comprises trinucleosomal ladder fractions.

18 The composition according to claim 14, wherein the second nucleosomal nucleic acid preparation comprises dinucleosomal ladder fractions.

19 The composition according to claim 15, wherein the second nucleosomal nucleic acid preparation comprises trinucleosomal ladder fractions.

20 A composition according to claim 2, wherein the primary cell source is blood cells from a buffy coat layer.

21 The composition of claims 1-19, wherein the amount of the second nucleosomal nucleic acid preparation is less than 40% of the total nucleic acid in the composition.

22 The composition of claim 21, wherein the amount of the second nucleosomal nucleic acid preparation is less than 30% of the total nucleic acid in the composition.

23 The composition of claim 22, wherein the second nucleosomal nucleic acid preparation is less than 20% of the total nucleic acid in the composition.

24 The composition of claim 23, wherein the amount of the second nucleosomal nucleic acid preparation is less than 10% of the total nucleic acid in the composition.

25 The composition of claim 8, wherein the first cell source is the mother of the second cell source.

26 The composition of claim 8, wherein the first cell source is the father of the second cell source.

27 The composition of claim 8, wherein the first cell source is a sibling of the second cell source.

28 The composition of claim 8, wherein the second cell source is a cancerous cell and the first cell source is a non-cancerous cell.

29 The composition of claim 28, wherein the first cell source and the second cell source are derived from the same individual.

30 The composition of claim 29, wherein the first cell source and the second cell source are cultured cell lines.

31 The composition of claim 25, wherein the amount of the second nucleosomal nucleic acid preparation is less of the total nucleic acid in the composition.

32 The composition of claim 28, wherein the amount of the second nucleosomal nucleic acid preparation is less than 30% of the total nucleic acid in the composition.

33 The composition of claim 29, wherein the second nucleosomal nucleic acid preparation is less than 20% of the total nucleic acid in the composition.

34 The composition of claim 30, wherein the amount of the second nucleosomal nucleic acid preparation is less than 10% of the total nucleic acid in the composition.

35 The composition of claims 1-19, wherein the a first nucleosomal nucleic acid preparation is prepared by isolating nuclei from the first cell source and the second nucleic acid preparation is prepared by isolating nuclei from the second cell source.

36 The composition of claims 1-19, wherein the amount of the second nucleosomal nucleic acid preparation is less than 40% of the total nucleic acid in the composition.

37 The composition of claim 32, wherein the amount of the second nucleosomal nucleic acid preparation is less than 30% of the total nucleic acid in the composition.

38 The composition of claim 33, wherein the second nucleosomal nucleic acid preparation is less than 20% of the total nucleic acid in the composition.

39 The composition of claim 34, wherein the amount of the second nucleosomal nucleic acid preparation is less than 10% of the total nucleic acid in the composition.

40 The composition of claims 1-31, wherein the nucleosomal preparation is obtained the first cell source or the second cell source after apoptosis has been is induced in the cell source.

41 A method of making a cell-free nucleic acid diagnostic testing standard composition, comprising, mixing a
  a first nucleosomal nucleic acid preparation derived from a first cell source, and
  a second nucleosomal nucleic acid preparation from a second cell source,
  wherein the quantity of the first nucleic acid preparation is greater than the quantity of the second nucleic acid preparation.

42 The method according to claim 37, wherein the first nucleosomal nucleic acid preparation is derived from a primary cell source.

43 The method according to claim 37, wherein the first nucleosomal nucleic acid preparation is derived from a cell line.

44 A method according to claim 37, wherein the first cell source and the second cell source are cell lines.

45 A method according to claim 37, wherein the first cell source and the second cell source are primary cell sources.

46 The method of claim 37, wherein the first cell source is a primary cell source and the second cell source is a cell line.

47 The method of claim 37, wherein the second cell source is a primary cell source and the first cell source is a cell line.

48 The method according to claims 37-43, wherein the first cell source is genetically related to the second cell source.

49 The method according to claims 37-43, wherein the first nucleosomal nucleic acid preparation has been prepared with an endonuclease.

50 The method according to claims 37-43, wherein the first nucleosomal nucleic acid preparation has been prepared with a micrococcal endonuclease.

51 The method according to claims 37-43, wherein the first nucleosomal nucleic acid preparation has been prepared with an endonuclease.

52 The method according to claims 37-43, wherein the first nucleosomal nucleic acid preparation and the second nucleosomal nucleic acid are nucleosomal ladder fractions.

53 The method according to claim 48, wherein the first nucleosomal nucleic acid preparation and the second nucleosomal nucleic acid comprise mononucleosomal ladder fractions.

54 The method according to claim 49, wherein the first nucleosomal nucleic acid preparation comprises dinucleosomal ladder fractions.

55 The method according to claim 50, wherein the first nucleosomal nucleic acid preparation comprises trinucleosomal ladder fractions.

56 The method according to claim 51, wherein the second nucleosomal nucleic acid preparation comprises dinucleosomal ladder fractions.

57 The method according to claim 52, wherein the second nucleosomal nucleic acid preparation comprises trinucleosomal ladder fractions.

58 The method according to claim 50, wherein the second nucleosomal nucleic acid preparation comprises dinucleosomal ladder fractions.

59 The method according to claim 51, wherein the second nucleosomal nucleic acid preparation comprises trinucleosomal ladder fractions.

60 A method according to claim 38, wherein the primary cell source is blood cells from a buffy coat layer.

61 The method of claims 37-55, wherein the amount of the second nucleosomal nucleic acid preparation is less than 40% of the second nucleic acid preparation.

62 The method of claim 57, wherein the amount of the second nucleosomal nucleic acid preparation is less than 30% of the second nucleic acid preparation.

63 The method of claim 58, wherein the second nucleosomal nucleic acid preparation is less than 20% of the second nucleic acid preparation.

64 The method of claim 57, wherein the amount of the second nucleosomal nucleic acid preparation is less than 10% of the second nucleic acid preparation.

65 The method of claim 44, wherein the first cell source is the mother of the second cell source.

66 The method of claim 44, wherein the first cell source is the father of the second cell source.

67 The method of claim 44, wherein the first cell source is a sibling of the second cell source.

68 The method of claim 61, wherein the amount of the second nucleosomal nucleic acid preparation is less than 40% of the second nucleic acid preparation.

69 The method of claim 64, wherein the amount of the second nucleosomal nucleic acid preparation is less than 30% of the second nucleic acid preparation.

70 The method of claim 65, wherein the second nucleosomal nucleic acid preparation is less than 20% of the second nucleic acid preparation.

71 The method of claim 66, wherein the amount of the second nucleosomal nucleic acid preparation is less than 10% of the second nucleic acid preparation.

72 The method of claims 37-55, wherein the a first nucleosomal nucleic acid preparation is prepared by isolating nuclei from the first cell source and the second nucleic acid preparation is prepared by isolating nuclei from the second cell source. The method of claims 1-19, wherein the amount of the second nucleosomal nucleic acid preparation is less than of the total nucleic acid in the composition.

73 The method of claim 68, wherein the amount of the second nucleosomal nucleic acid preparation is less than 30% of the total nucleic acid in the composition.

74 The method of claim 69, wherein the second nucleosomal nucleic acid preparation is less than 20% of the second nucleic acid preparation.

75 The method of claim 70, wherein the amount of the second nucleosomal nucleic acid preparation is less than 10% of the total nucleic acid in the composition.

76 The method of claims 37-67, wherein the nucleic acid preparation is obtained the first cell source or the second cell source after apoptosis has been is induced in the cell source.

77 A prenatal nucleic acid proficiency testing standard composition, made by the methods of claims 37-72.

78 A kit for first prenatal proficiency testing, the kit comprising a prenatal nucleic acid proficiency testing standard composition and a second prenatal nucleic acid proficiency testing standard composition, wherein prenatal nucleic acid proficiency testing standard compositions are different from each other, and each of the prenatal nucleic acid proficiency testing standard compositions is according to claims 1-36.

What is claimed is:

1. A cell-free nucleic acid diagnostic proficiency testing standard composition for analyzing non-invasive prenatal genetic tests, comprising
    a set of at least two nucleosomal nucleic acid preparations,
    wherein the nucleosomal nucleic acid preparations in the set have a quantity of a first nucleosomal nucleic acid preparation from a first cell line derived from a first individual and a quantity of a second nucleosomal nucleic acid preparation from a second cell line derived from a second individual,
    wherein the first individual is a mother or father of the second individual and the first and second individuals have different copy numbers of at least one chromosome,
    and wherein the quantity of the second nucleosomal nucleic acid preparation as a percentage of the quantity of the first nucleosomal nucleic acid preparation plus the quantity of the second nucleosomal nucleic acid preparation is different for each of the nucleosomal nucleic acid preparations in the set.

2. The composition according to claim 1, wherein the first nucleosomal nucleic acid preparation and the second nucleosomal nucleic acid preparation comprise mononucleosomal ladder fractions.

3. The composition according to claim 2, wherein the first nucleosomal nucleic acid preparation further comprises dinucleosomal ladder fractions.

4. The composition of claim 1, wherein the quantity of the second nucleosomal nucleic acid preparation in each of the nucleosomal nucleic acid preparations in the set is less than 40% as a percentage of the quantity of the first nucleosomal nucleic acid preparation plus the quantity of the second nucleosomal nucleic acid preparation.

5. The composition of claim 1, wherein the first nucleosomal nucleic acid preparation is obtained after apoptosis has been induced in the first cell line and/or the second nucleosomal nucleic acid preparation is obtained after apoptosis has been induced in the second cell line.

6. The composition of claim 1, wherein the quantity of the second nucleosomal nucleic acid preparation in each of the nucleosomal nucleic acid preparations in the set is less than 5% as a percentage of the quantity of the first nucleosomal nucleic acid preparation plus the quantity of the second nucleosomal nucleic acid preparation.

7. The composition of claim 1, wherein the quantity of the second nucleosomal nucleic acid preparation in each of the nucleosomal nucleic acid preparations in the set is between about 1% and about 70% as a percentage of the quantity of the first nucleosomal nucleic acid preparation plus the quantity of the second nucleosomal nucleic acid preparation.

8. The composition of claim 1, wherein the quantity of the second nucleosomal nucleic acid preparation in each of the nucleosomal nucleic acid preparations in the set is between about 4% and about 40% as a percentage of the quantity of the first nucleosomal nucleic acid preparation plus the quantity of the second nucleosomal nucleic acid preparation.

9. The composition of claim 1, wherein the first individual or the second individual is aneuploid.

10. A method of making a cell-free nucleic acid diagnostic testing standard composition for analyzing non-invasive prenatal genetic tests, comprising
generating a set of at least two nucleosomal nucleic acid preparations,
wherein the nucleosomal nucleic acid preparations in the set are made by mixing a quantity of a first nucleosomal nucleic acid preparation derived from a first cell line derived from a first individual and a quantity of a second nucleosomal nucleic acid preparation derived from a second cell line derived from a second individual,
wherein the first individual is a mother or father of the second individual and the first and second individuals have different copy numbers of at least one chromosome,
and wherein the quantity of the second nucleosomal nucleic acid preparation as a percentage of the quantity of the first nucleosomal nucleic acid preparation plus the quantity of the second nucleosomal nucleic acid preparation is different for each of the nucleosomal nucleic acid preparations in the set.

11. The method according to claim 10, wherein the first nucleosomal nucleic acid preparation and the second nucleosomal nucleic acid comprise mononucleosomal ladder fractions.

12. The method according to claim 11, wherein the first nucleosomal nucleic acid preparation further comprises dinucleosomal ladder fractions.

13. The method of claim 10, wherein the quantity of the second nucleosomal nucleic acid preparation in each of the nucleosomal nucleic acid preparations in the set is less than 40% as a percentage of the quantity of the first nucleosomal nucleic acid preparation plus the quantity of the second nucleosomal nucleic acid preparation.

14. The method of claim 10, wherein the first nucleosomal nucleic acid preparation is obtained after apoptosis has been induced in the first cell line and/or the second nucleosomal nucleic acid preparation is obtained after apoptosis has been induced in the second cell line.

15. The method of claim 10, wherein the quantity of the second nucleosomal nucleic acid preparation in each of the nucleosomal nucleic acid preparations in the set is less than 5% as a percentage of the quantity of the first nucleosomal nucleic acid preparation plus the quantity of the second nucleosomal nucleic acid preparation.

16. The method of claim 10, wherein the quantity of the second nucleosomal nucleic acid preparation in each of the nucleosomal nucleic acid preparations in the set is between about 1% and about 70% as a percentage of the quantity of the first nucleosomal nucleic acid preparation plus the quantity of the second nucleosomal nucleic acid preparation.

17. The method of claim 10, wherein the quantity of the second nucleosomal nucleic acid preparation in each of the nucleosomal nucleic acid preparations in the set is between about 4% and about 40% as a percentage of the quantity of the first nucleosomal nucleic acid preparation plus the quantity of the second nucleosomal nucleic acid preparation.

18. The method of claim 10, wherein the first individual or the second individual is aneuploid.

* * * * *